(12) United States Patent
Carter et al.

(10) Patent No.: US 8,821,927 B2
(45) Date of Patent: Sep. 2, 2014

(54) PHARMACEUTICAL COMPOSITION

(75) Inventors: Barry Howard Carter, Kinston, NC (US); Dwayne A Campbell, Durham, NC (US)

(73) Assignee: SmithKline Beecham (Cork) Limited, Carrigaline, County Cork (IE)

( * ) Notice: Subject to any disclaimer, the term of this patent is extended or adjusted under 35 U.S.C. 154(b) by 1151 days.

(21) Appl. No.: 11/911,843

(22) PCT Filed: Apr. 18, 2006

(86) PCT No.: PCT/US2006/014447
§ 371 (c)(1),
(2), (4) Date: Oct. 18, 2007

(87) PCT Pub. No.: WO2006/113649
PCT Pub. Date: Oct. 26, 2006

(65) Prior Publication Data
US 2008/0206330 A1  Aug. 28, 2008

Related U.S. Application Data

(60) Provisional application No. 60/672,805, filed on Apr. 19, 2005.

(51) Int. Cl.
*A61K 9/20* (2006.01)
*A61K 31/517* (2006.01)
*A61K 31/519* (2006.01)
*A61K 9/28* (2006.01)

(52) U.S. Cl.
CPC ............. *A61K 9/2866* (2013.01); *A61K 31/519* (2013.01); *A61K 9/2027* (2013.01); *A61K 9/2059* (2013.01); *A61K 9/2054* (2013.01)
USPC ...................................... 424/465; 514/266.24

(58) Field of Classification Search
CPC . A61K 31/519; A61K 9/2027; A61K 9/2054; A61K 9/2059; A61K 9/2866; C07D 405/12; C07D 405/14
USPC ...................................... 424/465; 514/266.24
See application file for complete search history.

(56) References Cited

U.S. PATENT DOCUMENTS

| | | | |
|---|---|---|---|
| 5,506,248 A * | 4/1996 | Nikfar et al. | ............... 514/374 |
| 5,770,599 A | 6/1998 | Gibson | |
| 6,358,961 B1 | 3/2002 | Angibaud et al. | |
| 6,713,485 B2 | 3/2004 | Carter et al. | |
| 6,727,256 B1 | 4/2004 | Carter et al. | |
| 7,157,466 B2 | 1/2007 | McClure et al. | |

FOREIGN PATENT DOCUMENTS

| | | |
|---|---|---|
| EP | 0787722 | 6/1997 |
| WO | 9909016 | 2/1999 |
| WO | WO 02/02552 | 1/2002 |
| WO | WO2004/000094 | 12/2003 |

OTHER PUBLICATIONS

US Pharmacopeia; 2002; 2496-2499.
Gao, et al., Drug nanocrystals for the formulation of poorly soluble drugs and its application as a potential drug delivery systerm, J. Nanopart Res. 10:845-862 (2008).
Highlights of Prescribing Information for TYKERB® (lapatinib) tablets, Revised Aug. 2007 TKB:3PI.

* cited by examiner

*Primary Examiner* — Aradhana Sasan
(74) *Attorney, Agent, or Firm* — J. Scott Young

(57) ABSTRACT

Oral pharmaceutical formulations containing ditosylate salts of 4-quinazolineamines are described as well as methods of using the same in the treatment of disorders characterized by aberrant erbB family PTK activity.

1 Claim, No Drawings

PHARMACEUTICAL COMPOSITION

CROSS REFERENCE TO RELATED APPLICATIONS

This application is filed pursuant to 35 U.S.C. §371 as a United States National Phase Application of International Application No. PCT/US2006/014447 filed Apr. 18, 2006, which claims priority from U.S. Provisional Patent Application No. 60/672,805, filed Apr. 19, 2005.

FIELD OF THE INVENTION

The present invention relates to pharmaceutical compositions containing, as an active ingredient, 4-quinazolinamines as well as use of the compositions in the treatment of proliferative diseases such as cancer. In particular, the pharmaceutical compositions contain at least one 4-quinazolinamine active ingredient that is an inhibitor of EGFR and/or erbB2 protein tyrosine kinase.

BACKGROUND OF THE INVENTION

Pharmaceutically active compounds may be formulated for administration by numerous routes. Typically, the appropriate route will depend on the disease being treated, the chemical and physical properties of the pharmaceutically active substance as well as the subjects to be treated. Suitable pharmaceutical formulations include those for oral, rectal, nasal, topical (including buccal, sub-lingual, and transdermal), vaginal or parenteral (including intramuscular, subcutaneous, intravenous, and directly into the affected tissue) administration or in a form suitable for administration by inhalation or insufflation. Pharmaceutical compositions for the treatment of cancer typically have been injectable, parenteral formulations for intravenous infusion of the pharmaceutically active compound. Generally, use of intravenous formulation has been indicated because of the cytotoxic nature of the anticancer formulation and/or the weakened condition of the patient. Anti-cancer solid dosage forms have been available in tablet form, for example Alkeran®, Leukeran®, Myleran®, Purinethol®, Tabloid®, and recently Xeloda®, but these have been the exception rather than the norm.

Tablets offer several advantages to both the manufacturer and to the patient. Tablets may be manufactured economically and are conveniently shipped, stored and dispensed. The patient can take advantage of a dosage form, which can be produced with an accurate dosage and has ease of administration and portability.

4-Quinazolinamines as dual inhibitors of the protein tyrosine kinases EGFR (Epithelial Growth Factor Receptor—also known as erbB-1) and erbB-2 have been disclosed in International Patent Application PCT/EP99/00048 filed Jan. 8, 1999, and published as WO 99/35146 on Jul. 15, 1999. The anhydrous and monohydrate ditosylate forms of specific 4-quinazolinamines were disclosed in International Patent Application PCT/US01/20706 filed Jun. 28, 2001, and published as WO 02/02552 on Jan. 10, 2002.

Of particular interest is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate. This compound is now in development as GW572016 in the treatment of various cancers, including breast, lung, bladder, head and neck, and gastric cancers. GW572016 has poor flow characteristics and is poorly soluble in aqueous media over the physiologically relevant pH range. Typically, for a pharmaceutical composition containing a drug having poor solubility in water and a high drug load, it is difficult to maintain the high dissolution properties and good flow characteristics needed for typical pharmaceutical manufacturing processes. Further, due to the poorly soluble active ingredient, high drug dissolution is required to achieve acceptable bioavailability. The present inventors have now identified a novel oral pharmaceutical formulation containing as an active ingredient a 4-quinazolinamine, which is effective as an EGFR and/or erbB2 protein tyrosine kinase inhibitor. Such a pharmaceutical formulation produced by fluid bed granulation provides high drug dissolution while maintaining good flow characteristics during processing.

DISCLOSURE OF THE INVENTION

In a first aspect of the present invention, there is provided an oral pharmaceutical composition, comprising (i) an active ingredient selected from a compound of formula (I),

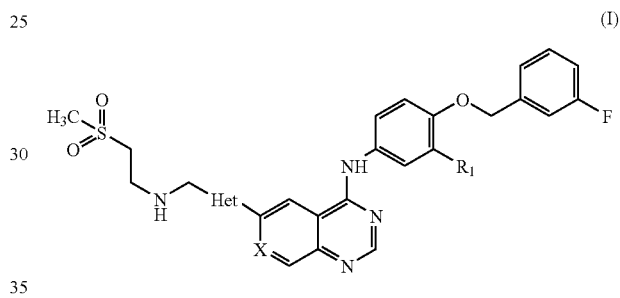

or salts or solvates thereof, wherein $R_1$ is Cl or Br; X is CH, N, or CF; and Het is thiazole or furan; and (ii) a binder.

In a second aspect of the present invention, there is provided an oral pharmaceutical composition, comprising (i) an active ingredient selected from a compound of formula (I),

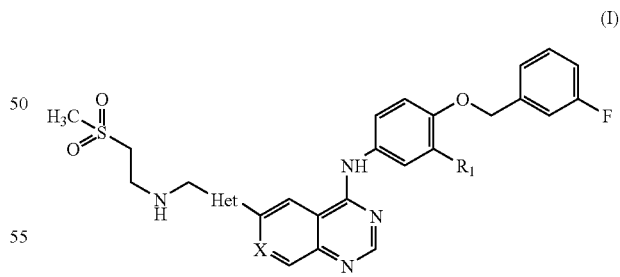

or salts or solvates thereof, wherein $R_1$ is Cl or Br; X is CH, N, or CF; and Het is thiazole or furan;

(ii) at least one binder; and (iii) at least one disintegrant.

In a third aspect of the present invention, there is provided an oral pharmaceutical composition, comprising (i) an active ingredient selected from a compound of formula (I),

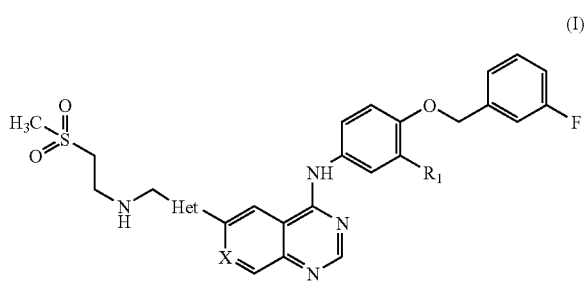

or salts or solvates thereof, wherein $R_1$ is Cl or Br; X is CH, N, or CF; and Het is thiazole or furan;
(ii) at least one binder;
(iii) at least one disintegrant; and
(iv) at least one lubricant.

In a fourth aspect of the present invention, there is provided an oral pharmaceutical composition, comprising
(i) an active ingredient selected from a compound of formula (I),

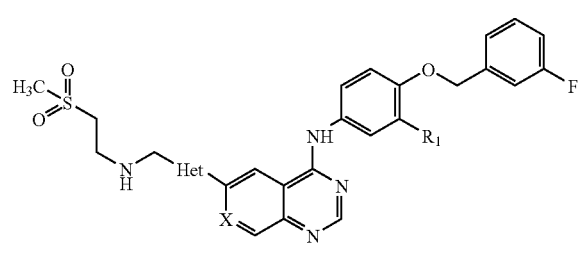

or salts or solvates thereof, wherein $R_1$ is Cl or Br; X is CH, N, or CF; and Het is thiazole or furan;
(ii) at least one binder;
(iii) at least one disintegrant;
(iv) at least one lubricant; and
(v) at least one diluent.

In a fifth aspect of the present invention, there is provided a method of treating a disorder in a mammal, said disorder being characterized by aberrant activity of at least one erbB family PTK, including: administering to said mammal an oral pharmaceutical composition, comprising
(i) an active ingredient selected from a compound of formula (I),

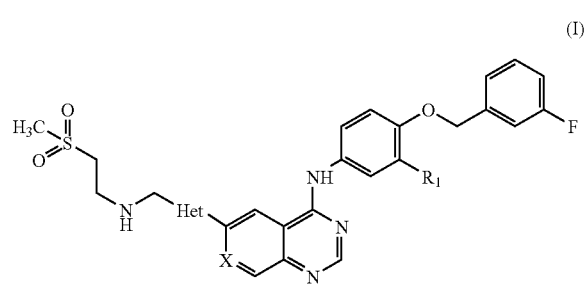

or salts or solvates thereof, wherein $R_1$ is Cl or Br; X is CH, N, or CF; and Het is thiazole or furan; and
(ii) a binder.

In a sixth aspect of the present invention, there is provided a method of treating a disorder in a mammal, said disorder being characterized by aberrant activity of at least one erbB family PTK, including: administering to said mammal an oral pharmaceutical composition, comprising
(i) an active ingredient selected from a compound of formula (I),

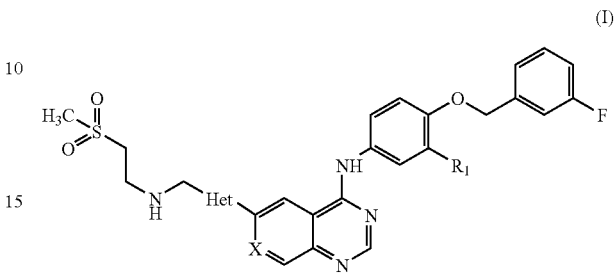

or salts or solvates thereof, wherein $R_1$ is Cl or Br; X is CH, N, or CF; and Het is thiazole or furan;
(ii) at least one binder; and
(iii) at least one disintegrant.

In a seventh aspect of the present invention, there is provided an oral pharmaceutical composition, comprising
(i) an active ingredient selected from a compound of formula (I),

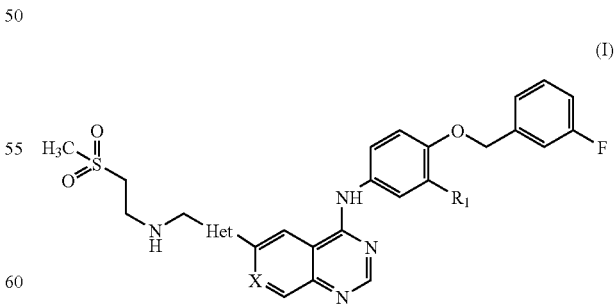

or salts or solvates thereof, wherein $R_1$ is Cl or Br; X is CH, N, or CF; and Het is thiazole or furan; and
(ii) a binder,
for use in therapy.

In a eighth aspect of the present invention, there is provided an oral pharmaceutical composition, comprising
(i) an active ingredient selected from a compound of formula (I), or salts or solvates thereof, wherein $R_1$ is Cl or Br; X is CH, N, or CF; and Het is thiazole or furan;
(ii) at least one binder; and
(iii) at least one disintegrant;
for use in therapy.

In an ninth aspect of the present invention, there is provided an oral pharmaceutical composition, comprising
(i) an active ingredient selected from a compound of formula (I),

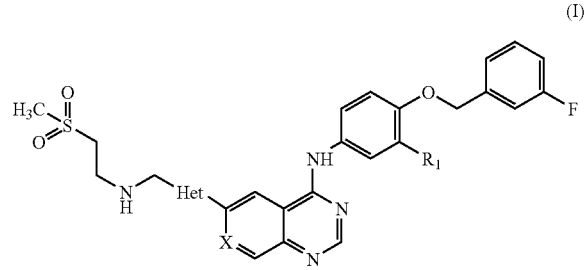

(I)

or salts or solvates thereof, wherein $R_1$ is Cl or Br; X is CH, N, or CF; and Het is thiazole or furan;
(ii) at least one binder;
(iii) at least one disintegrant;
(iv) at least one lubricant;
for use in therapy.

In a tenth aspect of the present invention, there is provided an oral pharmaceutical composition, comprising
(i) an active ingredient selected from a compound of formula (I),

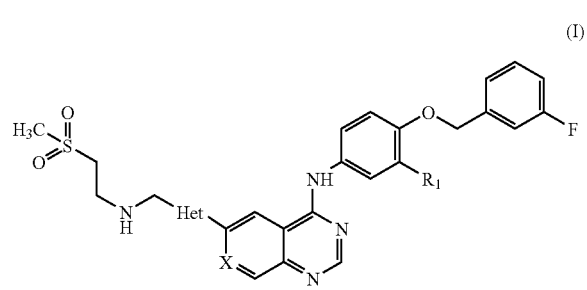

(I)

or salts or solvates thereof, wherein $R_1$ is Cl or Br; X is CH, N, or CF; and Het is thiazole or furan;
(ii) at least one binder;
(iii) at least one disintegrant;
(iv) at least one lubricant; and
(v) at least one diluent
for use in therapy.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "optionally" means that the subsequently described event(s) may or may not occur, and includes both event(s), which occur, and events that do not occur.

As used herein, the term "solvate" refers to a complex of variable stoichiometry formed by a solute (in this invention, a compound of formula (I), (II), (III), (IV) or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein the term "core tablet" is defined as a tablet without a film coating. Accordingly, as used herein the term "tablet" is defined as the core tablet with a film coating.

As used herein the term "PTK" means protein tyrosine kinase.

As used herein the term "EP" means European Pharmacopeia; the term "USP" means United States Pharmacopeia; the term "NF" means National Formulary, the term "JP" means Japanese Pharmacopeia; and the term "JPE" Japanese Pharmaceutical Excipients.

It is to be understood that the following embodiments refer to compounds within the scope of formula (I) and formula (II), (III), or (IV) as defined herein unless specifically limited by the definition of each formula or specifically limited otherwise. It is also understood that the embodiments of the present invention, including uses, compositions, and processes for making, described herein, while being described with regard to compounds of formula (I) are applicable to compounds of formulae (II), (III), and (IV).

Oral Pharmaceutical Composition

As recited above, the oral pharmaceutical composition of the present invention includes an active ingredient, which is selected from a compound of formula (I)

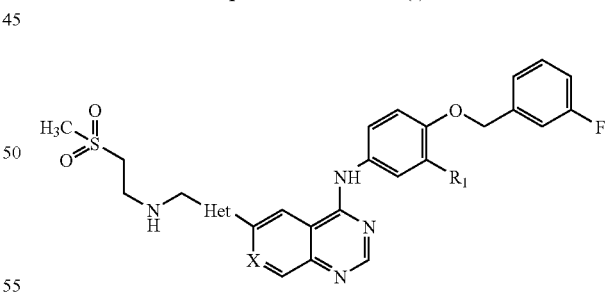

or a salt or solvate thereof, where $R_1$ is Cl or Br; X is CH, N, or CF; and Het is furan or thiazole.

The side chain $CH_3SO_2CH_2CH_2NHCH_2$ of the compounds of formula (I) may be linked to any suitable position of the group Het. Similarly, the phenyl group of the quinazoline core may be linked to any suitable position of the group Het.

In one embodiment, $R_1$ is Cl; X is CH; and Het is furan; preferably a compound of Formula (II) or salts or solvates thereof.

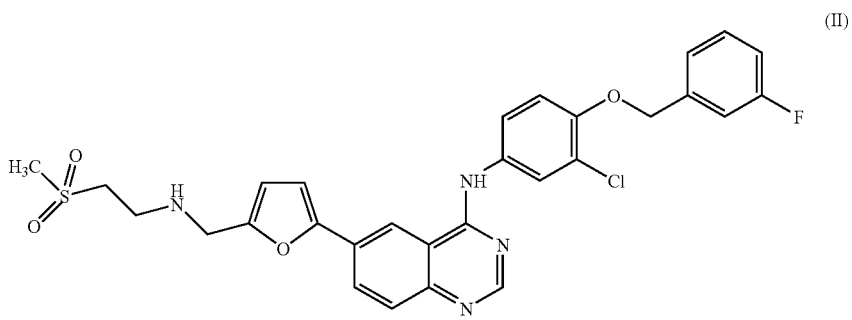 [SMILES: CS(=O)(=O)CCNCc1ccc(-c2ccc3ncnc(Nc4ccc(OCc5cccc(F)c5)c(Cl)c4)c3c2)o1]

(II)

The compound of formula (II) has the chemical name N-{3-Chloro-4-[(3-fluorobenzyl)oxy]phenyl}-6-[5-({[2-(methanesulphonyl)ethyl]amino}methyl)-2-furyl]-4-quinazolinamine and is designated GW572016.

In one embodiment, the compound is the ditosylate salt of the compound of formula II. In another embodiment, the compound is the monohydrate form of the ditosylate salt of formula (II). In another embodiment, the compound is the anhydrate form of the ditosylate salt of the compound of formula (II).

In an alternative embodiment, $R_1$ is Cl; X is CH; and Het is thiazole; preferably a compound of formula (III) or salts or solvates thereof.

The compound of formula (IV) is (4-(3-Fluoro-benzyloxy)-3-bromophenyl)-(6-(5-((2-methanesulphonyl-ethylamino)-methyl)-furan-2-yl)quinazolin-4-yl)-amine. In one embodiment, the compound is the ditosylate salt of the compound of formula III.

The compounds of formula (I), including the compounds of formulae (II), (III), and (IV), include within their scope substantially pure anhydrate or hydrate forms, as well as mixtures of hydrate and anhydrate forms. It is also understood, that such compounds include crystalline or amorphous forms and mixtures of crystalline and amorphous forms.

The active ingredient is present in a range of 5 to 85, preferably 30 to 60 more preferably 42 to 48 percent by

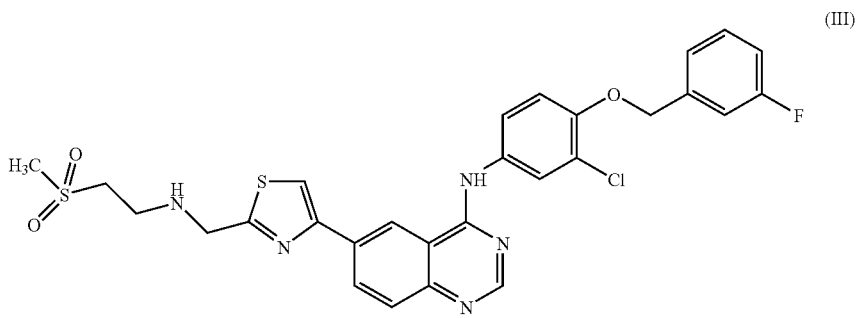 [SMILES: CS(=O)(=O)CCNCc1ccc(-c2ccc3ncnc(Nc4ccc(OCc5cccc(F)c5)c(Br)c4)c3c2)o1]

(III)

The compound of formula III is (4-(3-Fluoro-benzyloxy)-3-chlorophenyl)-(6-(2-((2-methanesulphonyl-ethylamino)-methyl)-thiazol-4-yl)quinazolin-4-yl)-amine. In one embodiment, the compound is the ditosylate salt of the compound of formula III.

In a further alternative embodiment, $R_1$ is Br; X is CH; and Het is furan; preferably, a compound of formula (IV) or salts or solvates thereof.

weight or 45-51 percent by weight of the oral pharmaceutical composition. In one embodiment, the active ingredient is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 5 to 85, preferably 30 to 60 more preferably 42 to 48 percent by weight or 45-51 percent by weight of the oral pharmaceutical composition.

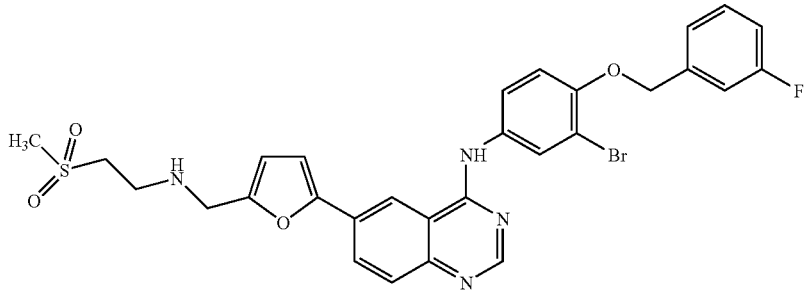

(IV)

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

The free base and HCl salts of the compounds of Formulae (I), (II), (III), and (IV), may be prepared according to the procedures of International Patent Application No. PCT/EP99/00048, filed Jan. 8, 1999, and published as WO 99/35146 on Jul. 15, 1999, referred to above. A schematic of such procedures is presented in Scheme A following. The specific page references given are to WO 99/35146. The free base of the compound of formula II is used as an example of the general scheme.

Scheme A

Procedure A - Reaction of an amine with a bicyclic species containing a 4-chloropyrimidine ring (p. 55, lines 21-33, p. 69, lines 30-34 and p. 74 line 35 - p. 75, line 4).

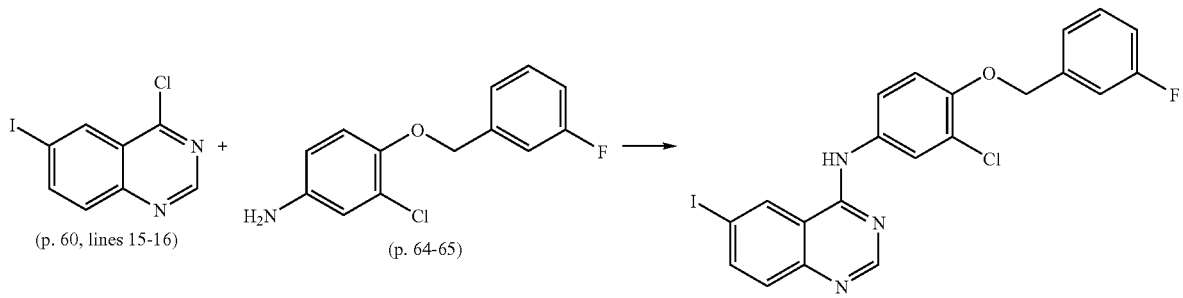

(p. 60, lines 15-16)    (p. 64-65)

Procedure B - Reaction of Procedure A product with heteroaryl tin reagent (p. 55, line 33 - p. 56, line 9)

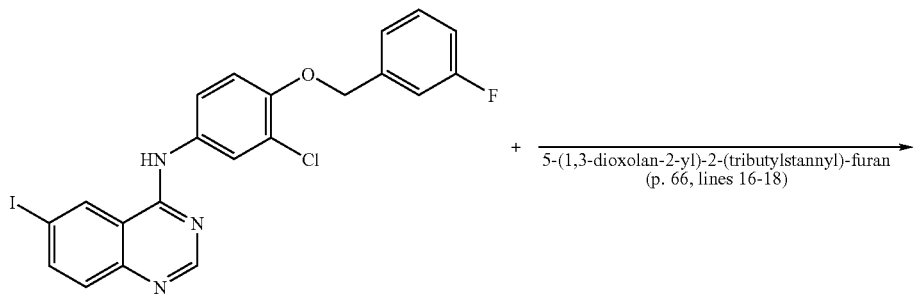

+ 5-(1,3-dioxolan-2-yl)-2-(tributylstannyl)-furan
(p. 66, lines 16-18)

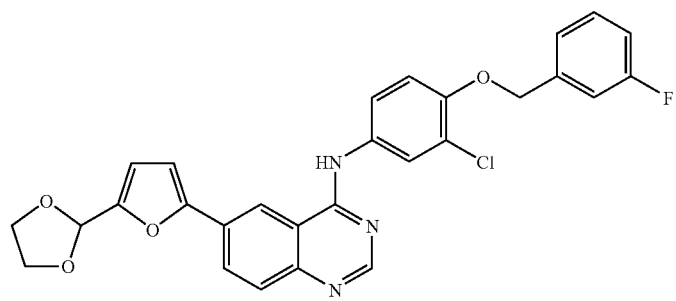

Procedure C - Removal of a 1,3-dioxolan-2yl protecting group to liberate an aldehyde (P. 56, lines 11-18)

-continued

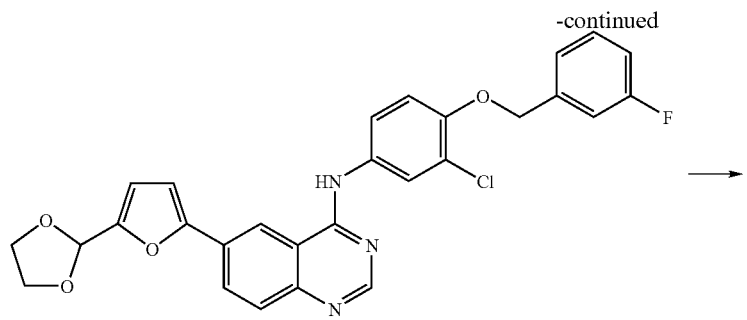

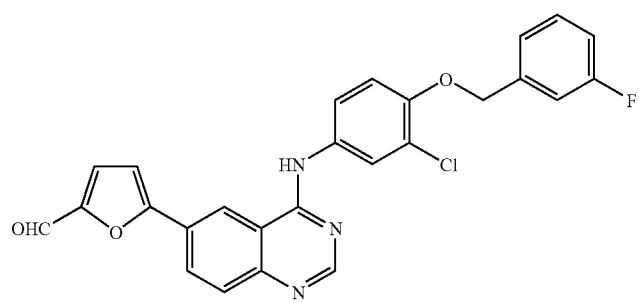

Procedure D - Reaction of an aldehyde with an amine by reductive animation (p. 56, lines 20-32; Example 29 - p. 100, lines 18-29)

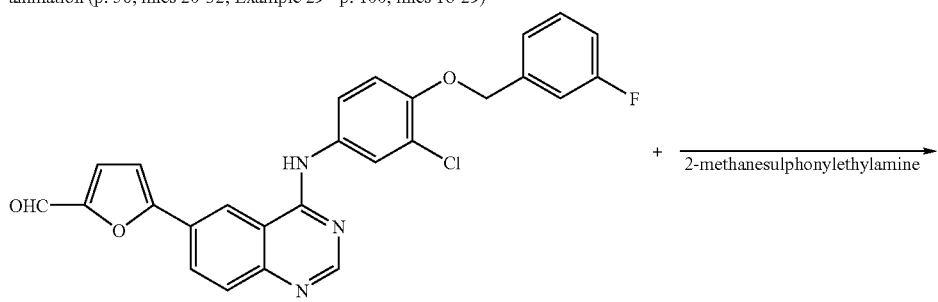

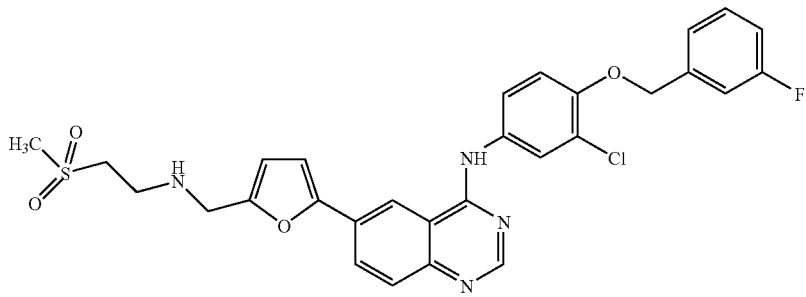

The ditosylate salts, including the anhydrous and hydrated forms thereof, of the compounds of Formulae (I), (II), (III), and (IV), may be prepared according to the procedures of International Patent Application No. PCT/US01/20706, filed Jun. 28, 2001, and published as WO 02/02552 on Jan. 10, 2002 and International; patent Application No. PCT/US03/10747, filed Apr. 8, 2003, and published as WO 03/086467 on Oct. 23, 2003. A further process is illustrated in Scheme B following.

Scheme B following illustrates the preparation of the ditosylate salt of the compound of formula (II). The preparation proceeds in four stages: Stage 1: reaction of quinazoline (I), which is prepared from 3H-6-iodoquinazolin-4-one (I'), with amine (II) to give iodoquinazoline (III); Stage 2: preparation of the corresponding aldehyde salt (V) by reaction of iodoquinazoline (III) and boronic acid (IV) followed by treatment with p-toluenesulfonic acid salt; Stage 3: preparation of the ditosylate salt of GW572016 (VI) from aldehyde salt (V); and Stage 4: recrystallization of the GW572016 ditosylate salt (VI). Scheme C shows an alternate preparation of the ditosylate salt of the compound of formula (II).

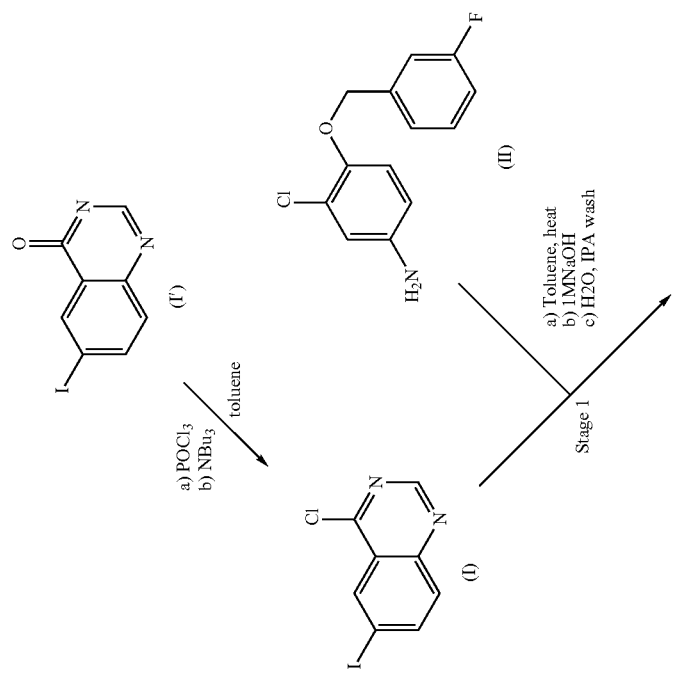

-continued
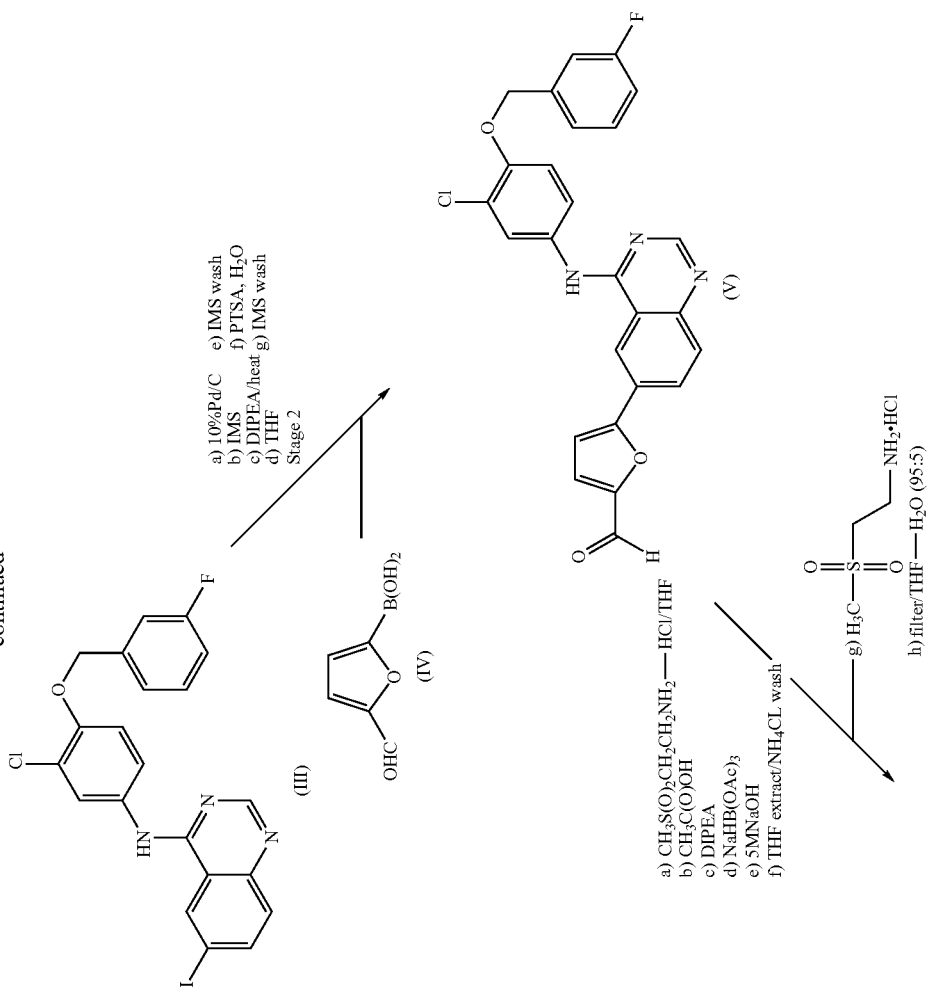

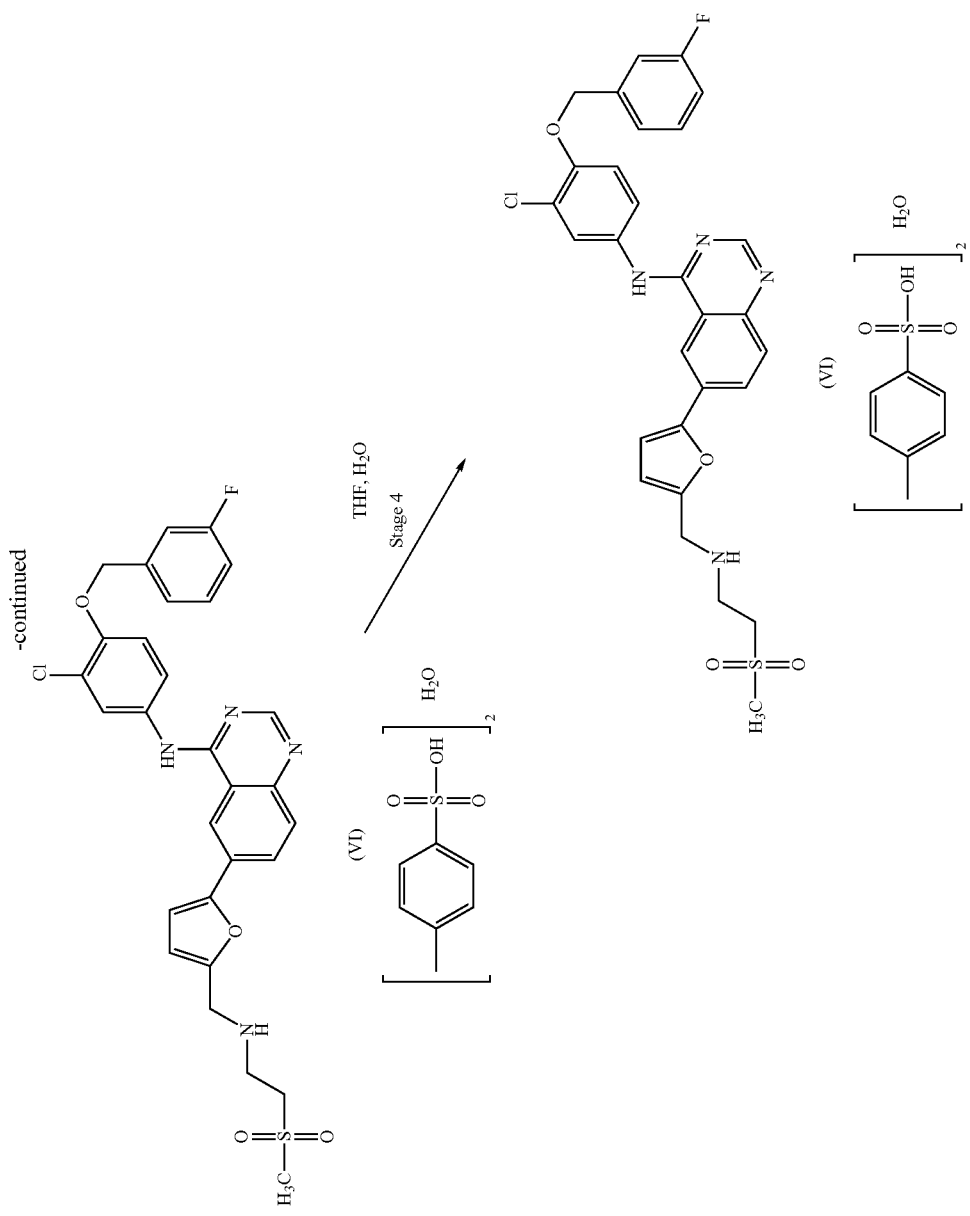

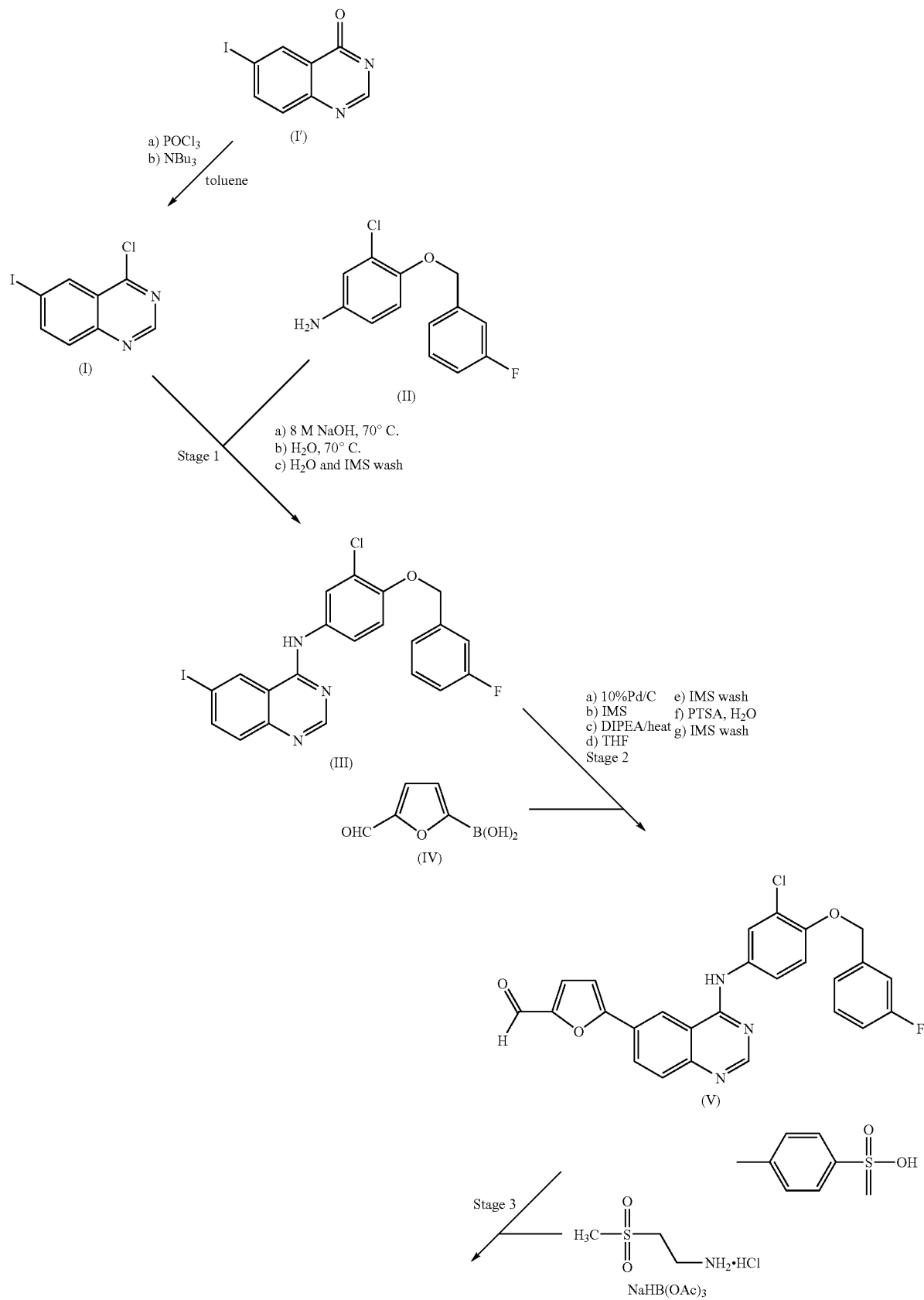

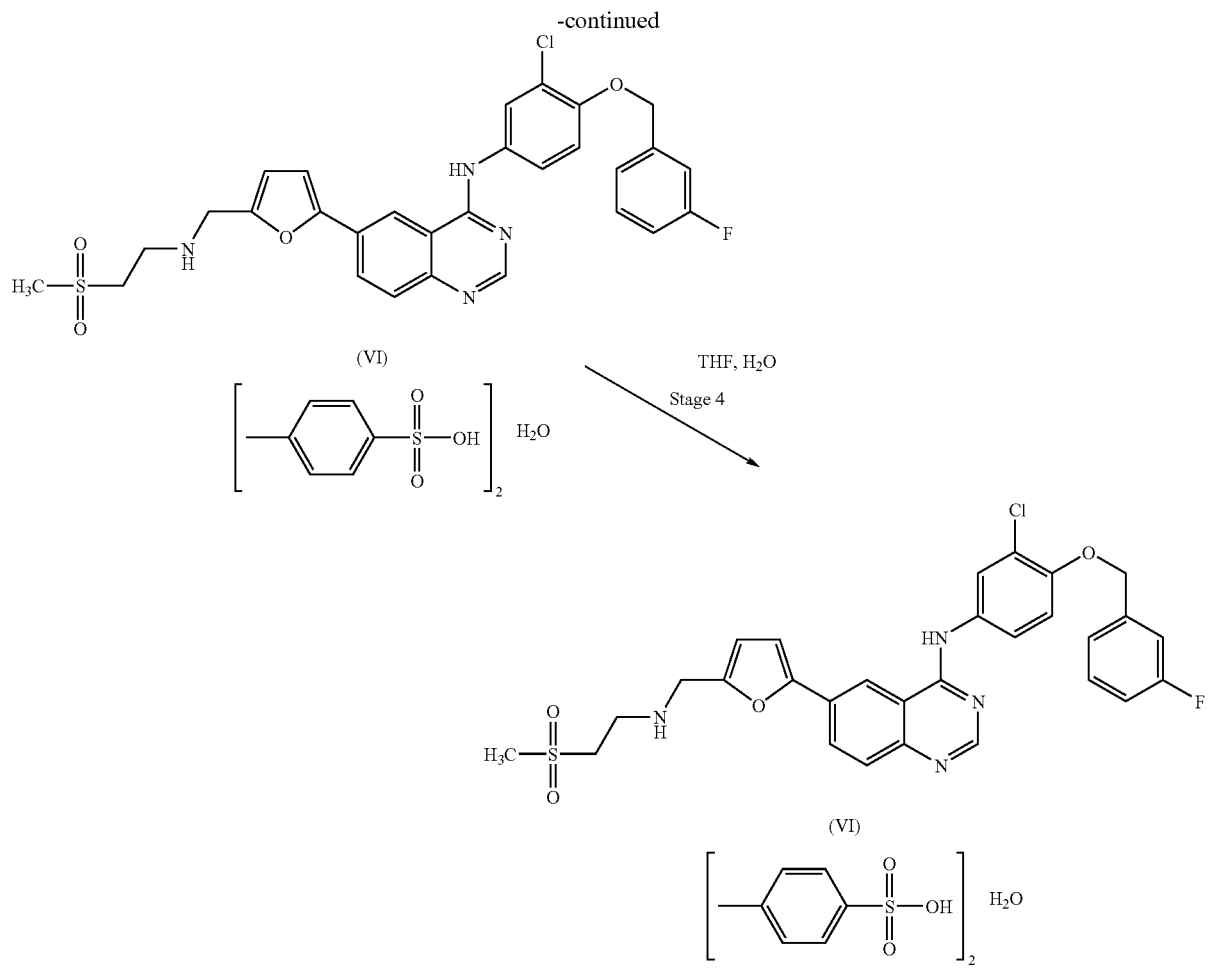

The oral pharmaceutical composition of the present invention also includes at least one binder. A binder is used to impart cohesiveness qualities to powdered materials so that tablets or granules formed will remain together and not fall apart. Any suitable binder that is compatible with the active ingredient and to good flow properties and dissolution may be utilized. Exemplary binders include, but are not limited to gelatin, starch, cellulose, cellulose derivatives such as methyl cellulose, hydroxylpropyl cellulose, hydroxypropylmethyl cellulose, ethyl cellulose, and carboxymethyl cellulose, sucrose, polyvinyl pyrrolidone, natural sugars such as glucose or beta-lactose, corn sweeteners, natural and synthetic gums such as acacia, tragacanth or sodium alginate, polyethylene glycol, waxes and the like.

In one embodiment, the at least one binder is polyvinyl pyrrolidone polymer or povidone, which is available from International Specialty Products of Wayne, N.J. as the Plasdone® line of products including Plasdone K-29/32®.

The at least one binder is present in a range of 2 to 11, preferably 4 to 9 more preferably 5.5 to 7.5 percent by weight of the oral pharmaceutical composition. In one embodiment, the binder is povidone, which is present in a range of 2 to 11, preferably 4 to 9 more preferably 5.5 to 7.5 percent by weight of the oral pharmaceutical composition.

The oral pharmaceutical composition of the present invention also includes at least one disintegrant. A disintegrant functions to ensure or facilitate the breakup or disintegration of the composition after administration thereby facilitating dissolution of the active substance. Any suitable disintegrant which is compatible with the active ingredient and to good flow properties and dissolution may be utilized. Exemplary disintegrants include, but are not limited to starch, cellulose and cellulose derivatives such as methyl cellulose, hydroxylpropyl cellulose, hydroxypropylmethyl cellulose, ethyl cellulose, and crosslinked sodium carboxymethyl cellulose, crosslinked polyvinyl pyrrolidone, sodium starch glycolate, agar, bentonite, and xanthan gum.

In one embodiment, the at least one disintegrant is sodium starch glycolate, which is available from DMV International of Veghel, The Netherlands as Primojel®. Primojel® is a purified sodium starch glycolate, Ph. Eur, USP/NF, JPE, produced by cross-linking and carboxymethylation of potato starch with subsequent purification. Sodium starch glycolate is also available from JRS Pharma of Patterson, N.Y. as the Explotab® or VivaStar® line of products including Explotab®, VivaStarP®, and Explotab CLV®.

It is understood by those skilled in the art that the disintegrant described above may be added into a tablet making process at two stages. Disintegrant can be added to the granulation mixture before granulation. This disintegrant is termed intra-granular disintegrant in that it becomes part of the granules formed. Disintegrant may also be added to the formed granules to form a compression mixture before compression. This disintegrant is termed extra-granular disintegrant in that it is not part of the granules, but rather is in mixture with the granules.

The at least one disintegrant is present in a range of 1 to 10, preferably 2 to 8 more preferably 3.5 to 5.5 percent by weight of the oral pharmaceutical composition. In one embodiment, the disintegrant is sodium starch glycolate, which is present in a range of 1 to 10, preferably 2 to 8 more preferably 3.5 to 5.5 percent by weight of the oral pharmaceutical composition. In one embodiment, the disintegrant is extra-granular disintegrant, which is present in a range of 1 to 10, preferably 2 to 8 more preferably 3.5 to 5.5 percent by weight of the oral pharmaceutical composition.

The oral pharmaceutical composition of the present invention may further comprise at least one diluent. A diluent or filler is used to increase the bulk of the composition so that the final product has a practical size or volume, for instance for a tablet a practical size for proper compression. Any suitable diluent that is compatible with the active ingredient and to good flow properties and dissolution may be utilized. Exemplary diluents include, but are not limited to lactose, sucrose or powdered sugar, mannitol, sorbitol, xylitol, inositol, calcium phosphate, calcium carbonate, calcium sulfate, dry starch, cellulose, including microcrystalline cellulose or silicified microcrystalline cellulose and the like.

In one embodiment, the at least one diluent is microcrystalline cellulose, which is available from Blanver, of Cotia, Brazil as the Tabulose® line of products including Tabulose® 101, 102, 103, 112, 250, 301, and 302; or from FMC of Philadelphia, Pa. as the Avicel® line of products including Avicel® PH 101, 102, 103, 105, 112, 113, 200, 301, and 302; or from JRS Pharma of Patterson, N.Y., which is available from as the Vivapur® line of products including Vivapur® 99, 101, 102, 103, 105, 112, 200, 301, and 302. In another embodiment, the at least diluent is silicified microcrystalline cellulose, which is available from JRS Pharma of Patterson, N.Y. as ProSolv® line of products.

The at least one diluent is present in a range of 10 to 70, preferably 35 to 50 more preferably 40 to 46 percent by weight of the oral pharmaceutical composition. In one embodiment, the diluent is microcrystalline cellulose, which is present in a range of 10 to 70, preferably 35 to 50 more preferably 40 to 46 percent by weight of the oral pharmaceutical composition. In one embodiment, the diluent is silicified microcrystalline cellulose, which is present in a range of 10 to 70, preferably 35 to 50 more preferably 40 to 46 percent by weight of the oral pharmaceutical composition.

The oral pharmaceutical composition of the present invention may further comprise at least one lubricant. A lubricant is used to prevent adhesion of material to the surface of dies and punches in tablet formation, reduce inter-particle friction, facilitate ejection of tablets from the die cavity, and may improve the flow characteristics of a powder or granules. Any suitable lubricant that is compatible with the active ingredient and to good flow properties and dissolution profile may be utilized. Exemplary lubricants include, but are not limited to talc, magnesium stearate, calcium stearate, zinc stearate, sodium stearyl fumarate, stearic acid, glyceryl behenate, hydrogenated vegetable oils, and polyethylene glycol.

In one embodiment, the at least one lubricant is magnesium stearate, which is available from Mallincrodkt Corporation of St. Louis, Mo.

The at least one lubricant is present in a range of 0.1 to 5, preferably 0.6 to 1.3 more preferably 0.8 to 1.2 percent by weight of the oral pharmaceutical composition. In one embodiment, the lubricant is magnesium stearate, which is present in a range of 0.1 to 5, preferably 0.6 to 1.3 more preferably 0.8 to 1.2 percent by weight of the oral pharmaceutical composition.

In one embodiment, the oral pharmaceutical composition is a core tablet composition.

In one embodiment, the core tablet composition of the present invention includes (i) an active ingredient that is selected from N-{3-Chloro-4-[(3-fluorobenzyl)oxy]phenyl}-6-[5-({[2-(methanesulphonyl)ethyl]amino}methyl)-2-furyl]-4-quinazolinamine, (4-(3-Fluoro-benzyloxy)-3-chlorophenyl)-(6-(2-((2-methane sulphonyl-ethylamino)-methyl)-thiazol-4-yl)quinazolin-4-yl)-amine or (4-(3-Fluoro-benzyloxy)-3-bromophenyl)-(6-(5-((2-methanesulphonyl-ethylamino)-methyl)-furan-2-yl)quinazolin-4-yl)-amine or salts or solvates thereof; (ii) at least one binder; and) at least one disintegrant.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) at least one binder; (iii) at least one disintegrant; and (iv) at least one diluent.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; and (iii) sodium starch glycolate.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; (iii) sodium starch glycolate; and (iv) microcrystalline cellulose.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; (iii) sodium starch glycolate; (iv) microcrystalline cellulose; and (v) magnesium stearate.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) at least one binder; (iii) at least one disintegrant; (iv) at least one diluent; and (v) at least one lubricant.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 5 to 85, preferably 30 to 60, more preferably 42 to 48 percent by weight; (ii) at least one binder, which is present in a range of 2 to 11, preferably 4 to 9, more preferably 5.5 to 7.5 percent by weight; (iii) at least one disintegrant, which is present in a range of 1 to 10, preferably 2 to 8, more preferably 3.5 to 5.5 percent by weight; (iv) at least one diluent, which is present in a range of 10 to 70, preferably 35 to 50, more preferably 40 to 46 percent by weight; and (v) at least one lubricant, which is present in a range of 0.1 to 5, preferably 0.6 to 1.3, more preferably 0.8 to 1.2 percent by weight of the core tablet composition.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 5 to 85 percent by weight; (ii) povidone, which is present in a range of 2 to 11 percent by weight; (iii) sodium starch glycolate, which is present in a range of 1 to 10 percent by weight; (iv) microcrystalline cellulose which may be present in a range of 10 to 70 percent by weight; and (v) magnesium stearate, which may be present in a range of 0.1 to 5 percent by weight of the core tablet composition.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 30 to 60 percent by weight; (ii) povidone, which is present in a range of 4 to 9 percent by weight; (iii) sodium starch glycolate, which is present in a range of 2 to 8 percent by weight; (iv) microcrystalline cellulose, which may be present in a range of 35 to 50 percent by weight; and (v) magnesium stearate, which may be present in a range of 0.6 to 1.3 percent by weight of the core tablet composition.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 42 to 48 percent by weight; (ii) povidone, which is present in a range of 5.5 to 7.5 percent by weight; (iii) sodium starch glycolate, which is present in a range of 3.5 to 5.5 percent by weight; (iv) microcrystalline cellulose, which may be present in a range of 40 to 46 percent by weight; and (v) magnesium stearate, which may be present in a range of 0.8 to 1.2 percent by weight of the core tablet composition.

In one embodiment, the core tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; (iii) sodium starch glycolate; (iv) microcrystalline cellulose; and (v) magnesium stearate.

The active ingredients disclosed herein have been shown to be effective inhibitors of EGFR and/or erbB2 kinases as well as having anti-tumour efficacy versus various cancer cell lines whose cells express EGFR and/or erbB2. See for instance the aforementioned International Patent Application No. PCT/EP99/00048, filed Jan. 8, 1999, and published as WO 99/35146 on Jul. 15, 1999; International Patent Application No. PCT/US01/20706, filed Jun. 28, 2001, and published as WO 02/02552 on Jan. 10, 2002; and International Patent Application No. PCT/US03/10747, filed on Apr. 8, 2003 and published as WO 03/086467 on Oct. 23, 2003, which applications are incorporated herein by reference to the extent that they disclose the biological activity of the active ingredients recited herein.

Accordingly, also provided in the present invention, is a method for treating a disorder in a mammal characterized by aberrant activity of at least one erbB family PTK which includes administering an oral pharmaceutical composition as described herein.

The aberrant PTK activity referred to herein is any erbB family PTK activity that deviates from the normal erbB family protein kinase activity expected in a particular mammalian subject. Aberrant erbB family PTK activity may take the form of, for instance, an abnormal increase in activity, or an aberration in the timing and or control of PTK activity. Such aberrant activity may result then, for example, from overexpression or mutation of the protein kinase leading to inappropriate or uncontrolled activation. Furthermore, it is also understood that unwanted PTK activity may reside in an abnormal source, such as a malignancy. That is, the level of PTK activity does not have to be abnormal to be considered aberrant, rather the activity derives from an abnormal source.

The oral pharmaceutical compositions of the present invention contain compounds of formula (I) or anhydrate or hydrated salt forms thereof that are inhibitors of one or more erbB family PTKs and as such have utility in the treatment of disorders in mammals which are characterized by aberrant PTK activity, particularly humans. In one embodiment of the present invention, the disorder treated is characterized by at least one erbB family PTK, selected from EGFR, c-erb-B2 and c-erb-B4, exhibiting aberrant activity. In another embodiment, the disorder treated is characterized by at least two erbB family PTKs selected from EGFR, c-erb-B2 and c-erb-B4, exhibiting aberrant activity. In one embodiment of the treatment method, the compounds of formula (I) or anhydrate or hydrate forms thereof inhibit at least one erbB family PTK, selected from EGFR, c-erb-B2 and c-erb-B4. In another embodiment of the treatment method, the compounds of formula I or anhydrate or hydrate forms thereof inhibit at least two erbB family PTKs selected from EGFR, c-erb-B2 and c-erb-B4.

The disorders referred to may be any disorder which is characterized by aberrant PTK activity. As recited above such disorders include, but are not limited to, cancer and psoriasis. In a preferred embodiment, the disorder is cancer. In a more preferred embodiment, the cancer is non-small cell lung, bladder, prostate, brain, head and neck, breast, ovarian, gastric, colorectal, or pancreatic cancer.

A therapeutically effective amount of a compound of formula (I) and anhydrate or hydrate forms thereof will depend on a number of factors including, but not limited to, the age and weight of the mammal, the precise disorder requiring treatment and its severity, the nature of the formulation, and the route of administration, and will ultimately be at the discretion of the attendant physician or veterinarian. Typically, the compounds of formula (I) and anhydrate or hydrate forms thereof will be given for treatment in the range of 0.1 to 100 mg/kg body weight of recipient (mammal) per day and more usually in the range of 1 to 50 mg/kg body weight per day. Acceptable daily dosages, may be from about 0.1 to about 2000 mg/day, and preferably from about 10 to about 1800 mg/day.

The oral pharmaceutical compositions containing compounds of formula (I) or anhydrate or hydrated salt forms thereof, described above, are useful in therapy.

The oral pharmaceutical composition of the present invention and at least one additional cancer treatment therapy may be employed in combination concomitantly or sequentially in any therapeutically appropriate combination with such other anti-cancer therapies. The additional anti-cancer therapy is typically selected from one or more of surgical, radiological, or chemotherapeutic therapies. In one embodiment, the additional anti-cancer therapy is at least one surgical therapy. In another embodiment, the additional anti-cancer therapy is at least one radiological therapy. In one embodiment, the additional anti-cancer therapy is at least one of surgical, radiological, or chemotherapeutic therapy. In one embodiment, the additional anti-cancer therapy is at least one chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds or salts, solvates or physiologically functional derivatives thereof of formula I include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; gemcitabine; fluoropyrimidines such as 5-fluorouracil and fluorodeoxyuridine; antimetabolites such as allopurinol, fludarabine, methotrexate, cladrabine, cytarabine, mercaptopurine and thioguanine; and camptothecins such as 9-amino camptothecin, irinotecan, topotecan, CPT-11 and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), insulin growth factor receptor (IGF-R1), vascular endothelial growth factor receptor (VEGFR, and TIE-2 (other than those VEGFR and TIE-2 inhibitors described in the present invention); and other tyrosine kinase inhibitors such as inhibitors of CDK2 and CDK4 inhibitors.

Additional description of these and additional anti-cancer therapies can be found in published US Application 2004/0053946A1 published Mar. 18, 2004 which is incorporated by reference herein to the extent that it teaches anti-cancer therapies.

In one embodiment, the oral pharmaceutical composition of the present invention is a tablet that is prepared using a fluid bed granulation process.

Accordingly, in one aspect of the present invention, there is provided a process for preparing a tablet, comprising:
(a) admixing and fluidizing the active ingredient and at least one diluent to form a fluidized mixture;
(b) granulating said mixture utilizing a granulating solution of at least one binder to form active granules;
(c) blending the active granules with a disintegrant;
(d) adding a lubricant to the active granule/disintegrant mixture and blending to form a compression blend; and
(e) forming tablets from the compression blend.

In another aspect of the present invention, there is provided a process for preparing a tablet, comprising:
(a) admixing and fluidizing the active ingredient and at least one diluent to form a fluidized mixture;
(b) granulating said mixture utilizing an aqueous solution of at least one binder to form active granules;
(c) blending the active granules with a disintegrant;
(d) adding a lubricant to the active granule/disintegrant mixture and blending to form a compression blend; and
(e) forming tablets from the compression blend.

In another aspect of the present invention, there is provided a process for preparing a tablet, comprising:
(a) admixing and fluidizing the active ingredient and at least one diluent to form a fluidized mixture;
(b) granulating said mixture utilizing a granulating solution of at least one binder to form active granules;
(c) blending the active granules with a disintegrant and at least one lubricant to form a compression blend;
(d) forming tablets from the compression blend; and
(e) film coating the tablets.

In another aspect of the present invention, there is provided a process for preparing a tablet, comprising:
(a) admixing and fluidizing the active ingredient and at least one diluent to form a fluidized mixture;
(b) granulating said mixture utilizing an aqueous solution of at least one binder to form active granules;
(c) blending the active granules with a disintegrant and at least one lubricant to form a compression blend;
(d) forming tablets from the compression blend; and
(e) film coating the tablets.

In another aspect of the present invention, there is provided a process for preparing a tablet, comprising:
(a) admixing and fluidizing the active ingredient, at least one diluent, and at least one binder to form a fluidized mixture;
(b) granulating said mixture utilizing a granulating solution to form active granules;
(c) blending the active granules with a disintegrant and at least one lubricant to form a compression blend;
(d) forming tablets from the compression blend; and
(e) film coating the tablets.

In another aspect of the present invention, there is provided a process for preparing a tablet, comprising:
(a) admixing and fluidizing the active ingredient, at least one diluent, and at least one binder to form a fluidized mixture;
(b) granulating said mixture utilizing a granulating solution to form active granules;
(c) blending the active granules with a disintegrant and at least one lubricant to form a compression blend;
(d) forming tablets from the compression blend; and
(e) film coating the tablets.

As recited above, the tablet forming process of the present invention includes a step (a) admixing the active ingredient and at least one diluent to form a granulation mixture. The admixing is done, for instance, in a fluid bed granulator by placing the active ingredient and diluent in the bowl of a GLATT® GPCG30 fluid bed granulator available from Glatt Air Technologies of Ramsey, N.J. or a GLATT® WSTCD 160/200 fluid bed granulator available from the Glatt Group of Companies of Binzen, Germany. The diluent may optionally be sieved prior to admixing with the active. If sieved, the diluent is sieved using a US Mesh sized 16, 20, or 24, preferably a 20 sieve. The admixed active and diluent are then fluidized in the GLATT® GPCG30 or GLATT® WSTCD 160/200 to form a fluidized mixture using standard process parameters known in the art.

Suitable active ingredients and diluents are as described above for the oral pharmaceutical composition.

In an alternative embodiment, step (a) includes admixing the active ingredient, at least one diluent, and at least binder to form a granulation mixture. The admixing is performed as recited above. Suitable active ingredients, diluents, and binders are as described above for the oral pharmaceutical composition.

Accordingly, in one embodiment, the fluidized mixture of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; and (ii) at least one diluent.

In one embodiment, the fluidized mixture of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 35 to 67, preferably 45 to 57 percent by weight; and (ii) at least one diluent which is present in a range of 33 to 65, preferably 43 to 55 percent by weight of the fluidized mixture.

In another embodiment, the fluidized mixture of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; and (ii) microcrystalline cellulose.

In a further embodiment, the fluidized mixture of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 35 to 67, preferably 45 to 57 percent by weight; and (ii) microcrystalline cellulose which is present in a range of 33 to 65, preferably 43 to 55 percent by weight of the fluidized mixture.

After preparation, the fluidized mixture is granulated in step (b) using a granulating solution. The granulating solution may be an aqueous, non-aqueous or a aqueous/non-aqueous solution. The solution may or may not include the at least one binder. That is, the granulating solution may be an aqueous, non-aqueous, or an aqueous/non-aqueous solution of the at least one binder or in another embodiment, the at least one binder is included in the fluidized mixture and the granulating solution is water, a non-aqueous liquid, or an aqueous/non-aqueous liquid. The aqueous solution is of course water or a water solution with the at least one binder. The non-aqueous solution includes, but is not limited to, alcohols such as ethanol, or isopropanol; other organics such as acetone; or mixtures of alcohols or other organics such as an acetone/ethanol mixture, or acetone/isopropanol mixture; and the like with or without the at least one binder. The aqueous/non-aqueous solution is, but is not limited to, water/ethanol, water/acetone, or water/isopropanol mixtures with or without the at least one binder.

In one embodiment, the aqueous solution is a 5 to 25, preferably 10 to 25, more preferably a 15 to 25 percent solution of at least one binder in purified water (USP). Preferably, the aqueous solution is a 5 to 25, preferably 10 to 25, more preferably 15 to 25 percent solution of povidone in purified water (USP). The aqueous solution is prepared for instance in a suitable tank with a propeller type mixer such as a Lighting Mixer with suitable bowl. The aqueous mixture is sprayed onto the fluidized mixture after formation of the fluidized mixture at a rate adequate to insure proper granule formation. As is known in the art, the specific combination of batch size, inlet air temperature, inlet air dewpoint, and inlet air volume will determine acceptable binder solution spray rates. An additional amount of water may be added as needed to provide proper granulation wetness. At the end of granulation the inlet air temperature, may be raised to facilitate the drying process until an acceptable moisture content (such as Loss On Drying—LOD) is reached. The dried granules may be passed through, for instance, a cone mill, such as a Comil® available from Quadro Engineering Incorporated of Waterloo, Ontario, using an appropriate combination of screen size and impeller speed to produce the desired active granule product.

Accordingly, in one embodiment, the active granules of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) at least one diluent; and (iii) at least one binder.

In one embodiment, the active granules of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) microcrystalline cellulose; and (iii) povidone.

In one embodiment, the active granules of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 5 to 85, preferably 30 to 60, more preferably 45 to 51 percent by weight; (ii) at least one diluent, which is present in a range of 4 to 93, preferably 31 to 66, more preferably 41 to 49 percent by weight; and (iii) at least one binder, which is present in a range of 2 to 11, preferably 4 to 9, more preferably 6 to 8 percent by weight of the active granules.

In one embodiment, the active granules of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 5 to 85 percent by weight; (ii) microcrystalline cellulose, which is present in a range of 4 to 93 percent by weight; and (iii) povidone, which is present in a range of 2 to 11 percent by weight of the active granules.

In one embodiment, the active granules of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 30 to 60 percent by weight; (ii) microcrystalline cellulose, which is present in a range of 31 to 66 percent by weight; and (iii) povidone, which is present in a range of 4 to 9 percent by weight of the active granules.

In one embodiment, the active granules of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 45 to 51 percent by weight; (ii) microcrystalline cellulose, which is present in a range of 41 to 49 percent by weight; and (iii) povidone which is present in a range of 6 to 8 percent by weight of the active granules.

After preparation the active granules are blended in step (c) with at least one disintegrant and at least one lubricant to form a compression blend. The active granules may be first blended with the at least one disintegrant and then the active granules/disintegrant mixture blended with at least one lubricant to form a compression blend. Alternatively, the active granules, the at least one disintegrant, and the at least one lubricant are blended together to form the compression mixture.

The ingredients are blended, using for instance a V-Blender available from Granulair Technologies of Lausanne, Switzerland or BULS cube blender available from Matcon, Incorporated of Sewell, N.J., at low rpm until blend uniformity is achieved. As is recognized in the art, the time needed to achieve such uniformity will vary according to the amount and character of the ingredients and specific process equipment.

The components of the compression blend, i.e., the active granules, disintegrant, and lubricant are as described above.

In one embodiment, the compression blend of the present invention includes (i) active granules; (ii) at least one disintegrant; and (iii) at least one lubricant.

In one embodiment, the compression blend of the present invention includes (i) active granules which are present in a range of 85 to 99, preferably 87 to 91, more preferably 93 to 96 percent by weight; (ii) at least one disintegrant, which is present in a range of 1 to 10, preferably 2 to 8, more preferably 3.5 to 5.5 percent by weight; and (iii) at least one lubricant which is present in a range of 0.1 to 5, preferably 0.6 to 1.3, more preferably 0.8 to 1.2 percent by weight of the compression blend.

In one embodiment, the compression blend of the present invention includes (i) active granules; (ii) sodium starch glycolate; and (iii) magnesium stearate.

In one embodiment, the compression blend of the present invention includes (i) active granules which are present in a range of 85 to 99 percent by weight; (ii) sodium starch glycolate, which is present in a range of 1 to 10 percent by weight; and (iii) magnesium stearate, which is present in a range of 0.1 to 5 percent by weight of the compression blend.

In one embodiment, the compression blend of the present invention includes (i) active granules which are present in a range of 87 to 91 percent by weight; (ii) sodium starch glycolate, which is present in a range of 2 to 8 percent by weight; and (iii) magnesium stearate, which is present in a range of 0.6 to 1.3 percent by weight of the compression blend.

In one embodiment, the compression blend of the present invention includes (i) active granules which are present in a range of 93 to 96 percent by weight; (ii) sodium starch glycolate, which is present in a range of 3.5 to 5.5 percent by weight; and (iii) magnesium stearate, which may be present in a range of 0.8 to 1.2 percent by weight of the compression blend.

Core tablets are formed from the compression blend (step (d)) by compressing the blend into tablet form. Any suitable means for tablet compression may be used, including, but not limited to, a single punch machine, rotary tablet machines and instrumented tablet machines. In one embodiment, the tableting is done by a rotary tablet machine, for instance a Hata model HT-AP18SSU rotary tablet press available from Elizabeth-Hata International of North Huntingdon, Pa. or William Fette GmbH of Schwarzenbek, Germany. The Hata press is fitted with a 19.05×10.41 mm standard concave tooling. In-process controls for uniformity of weight, average weight, hardness, friability, and disintegration time are applied during the compression run and adjustments to the tablet press are made if necessary. The composition of the core tablets are as described above.

The tablets may optionally be film coated (step (e)) by any suitable means. In one embodiment, the tablets are film coated using a coater such as a Compulab Accella Coata available from Thomas Engineering, Inc. of Hoffman Estates, Ill. or the Glatt Group of Companies of Binzen, Germany. Coating of the tablets will enhance patient acceptance and control dust. In one embodiment, the tablets are coated with 12 percent by weight aqueous suspension of Orange Opadry® YS-1-13065A aqueous suspension available from Colorcon, Incorporated of Westpoint, Pa.

In one embodiment, the tablets of the present invention are immediate release tablets containing 250 mg of N-{3-Chloro-4-[(3-fluorobenzyl)oxy]phenyl}-6-[5-({[2-(methanesulphonyl)ethyl]amino}methyl)-2-furyl]-4-quinazolinamine.

In another embodiment, the tablets of the present invention have an average dissolution of 80 percent or greater, preferably 85 percent or greater, more preferably 90 percent or greater drug dissolution after 45 minutes when evaluated using a USP Type II apparatus at 55 rpm paddle speed in 900 ml of 0.1N HCl containing 2% w/w Tween 80® at 37° C.

In one embodiment, a tablet of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) at least one binder; (iii) at least one disintegrant; and (iv) a film coat.

In one embodiment, a tablet of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) at least one binder; (iii) at least one disintegrant; (iv) at least one diluent; and (v) a film coat.

In one embodiment, a tablet of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) at least one binder; (iii) at least one disintegrant; (iv) at least one diluent; (v) a lubricant; and (vi) a film coat.

In one embodiment, a tablet of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; (iii) sodium starch glycolate; and (iv) a film coat.

In one embodiment, a tablet of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; (iii) sodium starch glycolate; (iv) microcrystalline cellulose; and (v) a film coat.

In one embodiment, a tablet of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; (iii) sodium starch glycolate; (iv) microcrystalline cellulose; (v) magnesium stearate, and (vi) a film coat.

In one embodiment, a tablet of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 5 to 85, preferably 30 to 60, more preferably 45 to 51 percent by weight; (ii) at least one binder, which is present in a range of 2 to 11, preferably 4 to 9, more preferably 5.5 to 7.5 percent by weight; (iii) at least one disintegrant, which is present in a range of 1 to 10, preferably 2 to 8, more preferably 3.5 to 5.5 percent by weight; (iv) at least one diluent, which is present in a range of 10 to 70, preferably 35 to 50, more preferably 40 to 46 percent by weight; (v) at least one lubricant, which is present in a range of 0.1 to 5, preferably 0.6 to 1.3, more preferably 0.8 to 1.2 percent by weight, and (vi) a film coat which is present in the range of 2.0 to 4, preferably 2.5 to 3.5, more preferably 2.8 to 3.2 percent by weight of the core tablet composition.

In one embodiment, a tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate; (ii) povidone; (iii) sodium starch glycolate; (iv) microcrystalline cellulose; (v) magnesium stearate; and (vi) a film coat.

In one embodiment, a tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 5 to 85 percent by weight; (ii) povidone, which is present in a range of 2 to 11 percent by weight; (iii) sodium starch glycolate, which is present in a range of 1 to 10 percent by weight; (iv) microcrystalline cellulose, which may be present in a range of 10 to 70 percent by weight; (v) magnesium stearate, which may be present in a range of 0.1 to 5 percent by weight; and (vi) a film coat which is present in a range of 2.0 to 4.0 percent by weight of the core tablet composition.

In one embodiment, a tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 30 to 47 percent by weight; (ii) povidone, which is present in a range of 4 to 9 percent by weight; (iii) sodium starch glycolate, which is present in a range of 2 to 8 percent by weight; (iv) microcrystalline cellulose, which may be present in a range of 35 to 50 percent by weight; (v) magnesium stearate, which may be present in a range of 0.6 to 1.3 percent by weight; and (vi) a film coat which is present in a range of 2.5 to 3.5 percent by weight of the core tablet composition.

In another embodiment, a tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 30 to 60 percent by weight; (ii) povidone, which is present in a range of 4 to 9 percent by weight; (iii) sodium starch glycolate, which is present in a range of 2 to 8 percent by weight; (iv) microcrystalline cellulose, which may be present in a range of 35 to 50 percent by weight; (v) magnesium stearate, which may be present in a range of 0.6 to 1.3 percent by weight; and (vi) a film coat which is present in a range of 2.5 to 3.5 percent by weight of the core tablet composition.

In one embodiment, a tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 42 to 48 percent by weight; (ii) povidone, which is present in a range of 5.5 to 7.5 percent by weight; (iii) sodium starch glycolate, which is present in a range of 3.5 to 5.5 percent by weight; (iv) microcrystalline cellulose, which may be present in a range of 40 to 46 percent by weight; (v) magnesium stearate, which may be present in a range of 0.8 to 1.2 percent by weight; and (vi) a film coat which is present in a range of 2.8 to 3.2 percent by weight of the core tablet composition.

In one embodiment, a tablet composition of the present invention includes (i) an active ingredient that is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate which is present in a range of 45 to 51 percent by weight; (ii) povidone, which is present in a range of 5.5 to 7.5 percent by weight; (iii) sodium starch glycolate, which is present in a range of 3.5 to 5.5 percent by weight; (iv) microcrystalline cellulose, which may be present in a range of 40 to 46 percent by weight; (v) magnesium stearate, which may be present in a range of 0.8 to 1.2 percent by weight; and (vi) a film coat which is present in a range of 2.8 to 3.2 percent by weight of the core tablet composition.

In addition to tablets, the composition according to the present invention may also be administered in the form of capsules, caplets, gelcaps, pills, and any other oral dosage forms known in the pharmaceutical art.

In one embodiment, the present invention includes a method of producing a ditosylate salt of a compound of Formula (I):

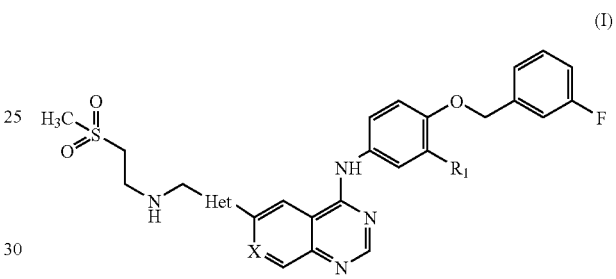

or salts or solvates thereof, wherein $R_1$ is Cl or Br; X is CH, N, or CF; and Het is thiazole or furan; wherein the method comprises the steps of:

(a) Reacting a compound of Formula (IV):

wherein X is CH, N, or CF with amine to give a compound of formula (V)

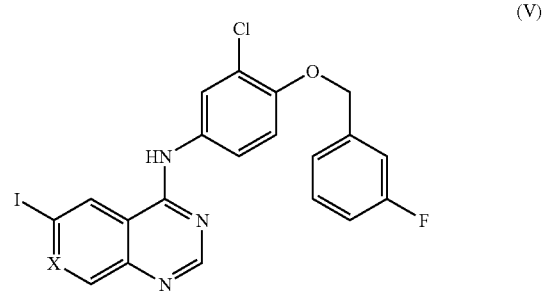

wherein X is CH, N, or CF (b) reacting the compound of formula (V) with boronic acid of formula (VI):

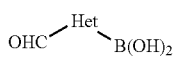
(VI)

where Het is thiazole or furan
followed by treatment with p-toluenesulfonic acid salt to form a compound of Formula (VII):

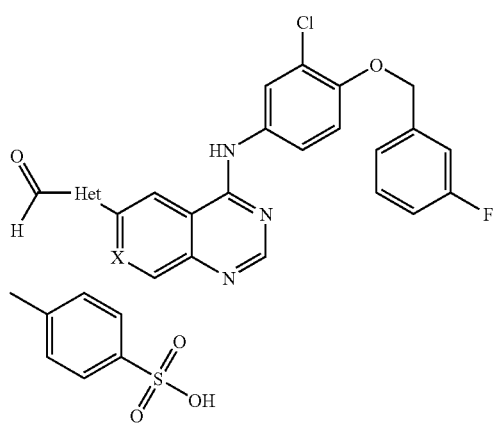
(VII)

where Het is thiazole or furan.
(c) preparing the ditosylate salt of a compound of formula (VII) to form a compound of formula (VIII):

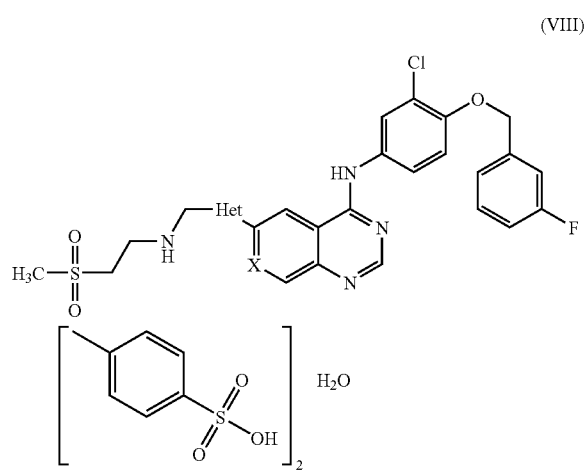
(VIII)

wherein X is CH, N, or CF and Het is thiazole or furan; and
(d) recrystallizing the compound of formula (VIII) prepared according to step (c) in the presence of tetrahydrofuran (THF).

In another embodiment, the invention encompasses a method of producing a ditosylate salt of a compound of Formula (I) where said method comprises the step of recrystallizing the compound of formula (VIII) is performed in the presence of at least 20 volumes of THF. In particular embodiments, the method comprises the step of recrystallizing the compound of formula (VIII) in the presence of at least 25 volumes of THF, at least 27 volumes of THF, or at least 30 volumes of THF.

The invention additionally provides methods of producing a ditosylate salt of a compound of formula (I) as described above wherein the compound is a compound of formula (II) or formula (III).

In a further embodiment, the invention encompasses a method of producing a ditosylate salt of an N-phenyl-4-quinazolinamine derivative where said method comprises the step of recrystallizing the N-phenyl-4-quinazolinamine derivative in the presence of at least 20 volumes of THF. In particular embodiments, the method comprises the step of recrystallizing the compound of formula (VIII) in the presence of at least 25 volumes of THF, at least 27 volumes of THF, or at least 30 volumes of THF. In one aspect, the N-phenyl-4-quinazolinamine derivative is N-(3-chloro-4-fluorophenyl)-7-(methyloxy)-6-{[3-(4-morpholinyl)propyl]oxy}-4-quinazolinamine.

The following examples are intended for illustration only and are not intended to limit the scope of the invention in any way. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| mm (millimeters); | kN: (kiloNewton) |
| cfm (cubic feet per minute) | kP (kilopond) |
| M (molar); | mM (millimolar); |
| N (Normal) | Kg (kilogram) |
| i.v. (intravenous); | mol (moles); |
| mmol (millimoles); | RT (room temperature); |
| min (minutes); | h (hours); |
| RSD (relative standard deviation) | rpm (revolutions per minute) |
| mp (melting point); | TLC (thin layer chromatography); |
| $T_r$ (retention time); | RP (reverse phase); |
| THF (tetrahydrofuran); | DMSO (dimethylsulfoxide); |
| EtOAc (ethyl acetate); | DME (1,2-dimethoxyethane); |
| DCM (dichloromethane); | DCE (dichloroethane); |
| DMF (N,N-dimethylformamide); | HOAc (acetic acid); |
| $POCl_3$ (phosphorus oxychloride); | $NBu_3$ (tri-n-butylamine); |
| MeOH (methanol); | IMS (industrial methylated spirit); |
| DIPEA (diisopropylethyleneamine); | PTSA (p-toluene sulfonic acid); |
| TMSE (2-(trimethylsilyl)ethyl); | TMS (trimethylsilyl); |
| TIPS (triisopropylsilyl); | TBS (t-butyldimethylsilyl); |

Unless otherwise indicated, all temperatures are expressed in ° C. (degrees Centigrade). All reactions conducted under an inert atmosphere at room temperature unless otherwise noted.

Example 1

Preparation of N-(3-chloro-4-[(3-fluorobenzyl)oxy]phenyl}-6-[5-({[2-(methane sulphonyl)ethyl]amino}methyl)-2-furyl]-4-quinazolinamine Tablets, 250 mg Table 1 contains a description of the components used in the preparation of a granulation mixture and Table 2 contains a description of the components used in the preparation of a compression blend for one embodiment of N-{3-Chloro-4-[(3-fluorobenzyl)oxy]phenyl}-6-[5-({[2-(methanesulphonyl)ethyl]amino}methyl)-2-furyl]-4-quinazolinamine Tablets, 250 mg for a batch size of 20,000 tablets.

TABLE 1

| Component | Amount (mg/tab)* | Amount (kg/batch)** | Function |
|---|---|---|---|
| Granulation Mixture | | | |
| Active[1] | 405 | 8.100 | Active |
| Microcrystalline Cellulose NF, PhEur, JP | 387 | 7.740 | Diluent Glidant |
| Povidone USP, PhEur, JP[2] | 58.5 | 1.170 | Binder |
| Purified Water[3] | qs | qs | Granulating liquid |
| Total dry granules | 850.5 | 17.01 | |

[1]N-{3-Chloro-4-[(3-fluorobenzyl) oxy]phenyl}-6-[5-({[2-(methanesulphonyl)ethyl] amino}methyl)-2-furyl]-4-quinazolinamine. Prepared according to the procedure of Scheme B. The actual amount of drug substance may be adjusted based on the purity of the specific lot of drug substance included in the batch. The amount of diluent (microcrystalline cellulose) is then adjusted to maintain a core tablet weight of 900 mg.
[2]Plasdone K29/32
[3]Removed during drying process.
*Based on theoretical drug substance factor of 1.62 = 1.00
**Quantities for a 20,000 tablet granulation.

TABLE 2

| Component | Amount (mg/tab) | Amount (kg/batch)* | Function |
|---|---|---|---|
| Compression Blend | | | |
| Granules[1] | 850.5 | 102.06 | Active Granules |
| Sodium Starch Glycolate[2] | 40.5 | 4.86 | Disintegrant |
| Magnesium Stearate | 9 | 1.08 | Lubricant |
| Total Weight | 900.0 | 108.0 | |
| Coating | | | |
| Opadry ®/Orange YS-1-13065-A | 27.0 | 3.24 | Film Coat |
| Purified Water[3] | qs | qs | |
| Total Tablet Weight | 927.0 | 111.24 | |

[1]Granules prepared from Granular Mix of Table 1
[2]Primojel NF, Pharm Eur, JPE
[3]Removed during drying process
*120000 Tablets For this example all ingredients were weighed to amounts which were consistent with the weight percents recited in Tables 1 and 2.

(i) Formation of Active Granules (Batch Size—120,000 Tablets)

N-{3-Chloro-4-[(3-fluorobenzyl)oxy]phenyl}-6-[5-({[2-(methanesulphonyl)ethyl]amino}methyl)-2-furyl]-4-quinazolin amine ditosylate monohydrate and microcrystalline cellulose NF, PH. Eur., JP were added to the bowl of a Glatt 30 granulator. A 10% solution of povidone in water was prepared using a Lightnin' mixer with a suitable tank. The N-{3-Chloro-4-[(3-fluorobenzyl)oxy]phenyl}-6-[5-({[2-(methanesulphonyl)ethyl]amino}methyl)-2-furyl]-4-quinazolin amine ditosylate monohydrate and microcrystalline cellulose were fluidized in the Glat 30 bowl and spraying of the 10% povidone solution began immediately at approximately 220 g/minute with an inlet air temperature of 54° C. The inlet air dewpoint was maintained between 10 to 15° C. After the povidone solution was applied purified water was added as needed to obtain a proper granulation wetness. At the end of granulation the inlet air temperature was raised to 60° C. and drying was continued until an LOD of approximately 2.5% was reached. The dried active granules were passed through a Comil Model 197S cone mill fitted with a 0.075 inch round holed screen at approximately 1720 RPM (28.6 Hz).

Sieve analysis was performed and tapped density profiles established. Sieve analysis was performed using a Retsch sieve shaker, Model AS200 Digit. Approximately 20 g of active dried granules was placed on the top of a nest of tared sieves of 20, 30, 40, 60, 100, and 200 mesh. Shaking was done for 5 minutes at an amplitude setting of 60 with the pulse on. This sieve analysis revealed little batch to batch variation in particle size of the active granules. The granules were also characterized for Bulk Density (BD) and Tapped Density (TD). BD and TD of the granules was measured by adding a weighed amount of granules into a 100 ml graduated cylinder and measuring the volume initially and after 25, 50, 200, 500, and 1250 taps respectively.

BD and TD showed minimal variation between batches.

(ii) Tablet Formation

A compression blend was formed by combining the prepared active granules and sodium starch glycolate in a bin which was transferred to a tumble blender where the ingredients were blended for 15 minutes @12 RPM. The bin was then removed from the tumble blender and magnesium stearate added to the blend of active granules and sodium starch glycolate. The bin was sealed and transferred back to the tumble blender and blended for 3 minutes @12 RPM to obtain the compression mix. Tablets were compressed from the compression blend using a Hata model HT-AP18SSU rotary tablet press fitted with 19.05×10.41 mm standard concave tooling. The tablet press was adjusted to provide tablets with the following specifications.

| | |
|---|---|
| Weight of 10 tablets | 9.00 g |
| Weight Range of 10 tablets | 8.80-9.20 g |
| Individual Tablet Weight | 900.0 mg |
| Individual Weight Range | 855.0-945.0 mg |
| Target Average Tablet Hardness | 18 kp |
| Individual Hardness Range | 9-27 kp |
| Individual Thickness Range | 5.00-8.00 mm |
| Compression Speed Range | 15-45 RPM |

Uncoated tablets were characterized for weight, hardness, disintegration and dissolution. Tablets were weighed and hardness determined using, for example, a Dr. Schleuniger® Pharmatron Testlink Instrument available from Dr Schleuniger® Pharmatron of Solothurn, Switzerland. Disintegration was determined in 1 L of water at 37° C. and drug dissolution was evaluated using a USP Type II apparatus at 55 rpm paddle speed in 900 ml of 0.1N HCl/2% w/w Tween 80 at 37° C. Results for three groups of tablets follow:

Average Weight:
1=900.2±1.23 mg; n=120
2=902.6±1.28 mg; n=90
3=901.8±0.99; n=60
Average Hardness:
1=18.6 kp
2=19.1 kp
3=18.6 kp
Disintegration:
1=2 min 2 seconds
2=1 minute 59 seconds
3=1 minute 57 seconds The produced tablets were coated in a Thomas Engineering Inc., Compu-Lab coater using 12% w/w Orange Opadry®NS-1-13065-A aqueous suspension at a pan speed of 6-8 rpm. Two spray nozzles (orifice opening-1.2 mm) were used to deliver coating solution at a total rate of 90-120 g/min. The airflow was maintained at 500 to 700 cfm with the outlet air temperature ranging from 50 to 63° C. The gun to bed distance was kept at 8.5 to 9 inches. Sufficient film coating was applied to achieve a 3 percent by weight gain assuming 100% coating efficiency.

Coated tablets were characterized for drug dissolution using a USP Type II apparatus at 55 rpm paddle speed in 900 ml of 0.1N HCl/2% w/w Tween 80 at 37° C. The results follow:

% Dissolution (45 min):
Range 81-95%
Average=#1=87
2=93
3=94

Table 3 recites the tablet composition.

TABLE 3

| Component | Amount (mg/tab)[2] | Reference to Standard | Function |
|---|---|---|---|
| Active[1] | 405 | | Active |
| Microcrystalline Cellulose | 387 | NF | Diluent |
| Povidone | 58.5 | EP, JP, USP | Binder |
| Purified Water[3] | qs | EP, JPE, NF | Granulating liquid |
| Sodium Starch Glycolate | 40.5 | EP, JP, USP | Disintegrant |
| Magnesium Stearate | 9.0 | EP, JPE, NF | Lubricant |
| Opadry ® YS-1-13065-A | 27 | EP[6], JPE, NF | Film coat |
| Purified Water[3] | qs | EP, JP, USP | Film coat solvent |
| Total tablet weight | 927 | | |

[1]N-{3-Chloro-4-[(3-fluorobenzyl) oxy]phenyl}-6-[5-({[2-(methanesulphonyl)ethyl]amino}methyl)-2-furyl]-4-quinazolinamine ditosylate monohydrate, equivalent to 250 mg [1]N-{3-Chloro-4-[(3-fluorobenzyl) oxy]phenyl}-6-[5-({[2-(methanesulphonyl)ethyl]amino}methyl)-2-furyl]-4-quinazolinamine.
[2]Theoretical core tablet weight is 900 mg.
[3]Removed during drying.

Example 2

Preparation of N-{3-Chloro-4-[(3-fluorobenzyl)oxy]phenyl}-6-[5-({[2-(methanesulphonyl)ethyl]amino}methyl)-2-furyl]-4-quinazolin amine ditosylate monohydrate N-{3-Chloro-4-[(3-fluorobenzyl)oxy]phenyl}-6-[5-({[2-(methanesulphonyl)ethyl]amino}methyl)-2-furyl]-4-quinazolin amine ditosylate monohydrate is prepared according to the procedure of Scheme C as follows:

Stage 1—A stirred suspension of 3H-6-iodoquinazolin-4-one in toluene (5 vols) is treated with tri-n-butylamine (1.2 equiv.), and then heated to 70-80° C. Phosphorous oxychloride (1.1 equiv.) is added and the reaction mixture is then heated to reflux and stirred at this temperature for at least 2 hours. The reaction mixture is then cooled to 55° C. and toluene (5-vol) added followed by 3-chloro-4-{[(3-fluorophenyl)methyl]oxy}aniline (1.03 equiv.). The reaction mixture is then warmed to 70-90° C. and stirred for at least 2 hours. The resultant slurry is transferred to a second vessel. The temperature is adjusted to 70-75° C. and 8 molar aqueous sodium hydroxide solution (2 vols) added over 1 hour, followed by water (6-vol.) maintaining the contents at 70-85° C. The mixture is stirred at 70-85° C. for ca. 1 hour and then cooled to 20-25° C. The suspension is stirred for ca. 2 hours and the product collected by filtration, and washed successively with water, 0.1 molar aqueous sodium hydroxide, water, and IMS, then dried in vacuo.

Stage 2—A mixture of N-(3-chloro-4-{[(3-fluorophenyl)methyl]oxy}phenyl)-6-iodo-4-quinazolinamine (1 wt), (5-formyl-2-furanyl)boronic acid (0.374 wt, 1.35 eq) and 10% Palladium on charcoal (0.028 wt 50% water wet) is slurried in ethanol (industrial methylated spirits, 15 vols) to give a grey suspension. The resultant slurry is stirred for 5 minutes and then treated with N,N-di-isopropylethylamine (0.396 vols, 1.15 eq.). The reaction slurry is heated to 70° C. for typically 3 hours when the reaction is complete (by HPLC analysis). The mixture is a thick green slurry at this point which is treated with THF (15 vols) to dissolve the product that has precipitated, leaving only the Pd/C catalyst out of solution. The mixture is then filtered hot through GFA filter to remove the catalyst. The vessel is rinsed with IMS (1 vol) and the wash used to rinse catalyst bed. A solution of p-toluenesulfonic acid monohydrate (1.50 wt, 4.0 eq.) in water (1.5 vols) is added to the filtered solution over 5 minutes at 65° C. The reaction solution is cooled to 60° C., with crystallization observed at 60-65° C. The resultant slurry is then stirred for at least 1 hour at 60° C. and then cooled to 20-25° C. and then held at this temperature for a further 1 hour. The product is isolated by filtration and the cake washed with IMS (3 vols). The product may be stored as a wet cake or dried.

Stage 3—5-{4-[(3-Chloro-4-{[(3-fluorophenyl)methyl]oxy}phenyl)amino]-6-quinazolinyl}-2-furancarbaldehyde 4-methylbenzenesulfonate (1 wt) and 2-(methylsulfonyl)ethylamine hydrochloride (0.4 wt, 1.60 equiv.) are suspended in THF (10 vols). Sequentially, acetic acid (0.354 vol., 4.00 equiv.) and di-isopropylethylamine (DIPEA, 1.08 vols, 4.00 equiv.) are added. The resulting solution is stirred at 30°-35° C. for ca. 1 hour then cooled to ca. 22° C. Sodium tri-acetoxyborohydride (0.66 wt, 2.00 equiv.) is then added. The resulting mixture is stirred at ca. 22° C. for 2-4 hours then sampled for HPLC analysis. The reaction is quenched by addition of aqueous sodium hydroxide (25% w/w, 3 vols) followed by water (2 vols.). The aqueous phase is then separated, extracted with THF (2 vols) and the combined THF extracts are then washed twice with 25% w/v aqueous ammonium chloride solution (2×5 vols). A solution of p-toluenesulfonic acid monohydrate (p-TSA, 0.74 wt, 2.5 equiv.) in water (1 vol) is prepared, warmed to ca. 60° C., and N-(3-chloro-4-{[(3-fluorophenyl)methyl]oxy}phenyl)-6-[5-({[2-(methylsulfonyl)ethyl]amino}methyl)-2-furanyl]-4-quinazolinamine 4-methylbenzenesulfonate hydrate seeds are added. The THF solution of the free base is added to the p-TSA solution over at least 1 hr, maintaining the batch temperature at 60±3° C. The resulting suspension is stirred at ca. 60° C. for 1-2 hours, cooled to 20-25° C. over an hour and aged at this temperature for ca. 1 hr. The solid is collected by filtration, washed with 95:5 THF: Water (3×2 vols) and dried in vacuum at ca. 35° C. to give N-(3-chloro-4-{[(3-fluorophenyl)methyl]oxy}phenyl)-6-[5-({[2-(methylsulfonyl)ethyl]amino}methyl)-2-furanyl]-4-quinazolinamine 4-methylbenzenesulfonate hydrate as a bright yellow crystalline solid.

Stage 4—A slurry of N-(3-chloro-4-{[(3-fluorophenyl)methyl]oxy}phenyl)-6-[5-({[2-(methylsulfonyl)ethyl]amino}methyl)-2-furanyl]-4-quinazolinamine 4-methylbenzenesulfonate hydrate (1.00 rel. wt) in aqueous tetrahydrofuran (80:20 THF: Water, 17 vols.) is heated to 63-64° C. and held for at least 30 min until a solution forms. The solution is clarified while hot and a line wash applied (80:20 THF: Water, 0.5 vol.). THF (15.5 vols) is added over ca. 1 hour whilst maintaining the temperature at 60-63° C. and the solution seeded with GW572016F (0.002 rel. wt). The batch is maintained at 60-63° C. for at least 30 minutes to allow crystallization to become established. The batch is cooled to ca. 5° C. over ca. 2 hours and the product isolated by filtration. It is washed twice with aqueous THF (90:10 THF: Water, 2×2 vols.) followed once with aqueous THF (19:1 THF: Water, 1×2 vols.). The batch is dried under vacuum up to 45° C. to give N-(3-chloro-4-{[(3-fluorophenyl)methyl]oxy}phenyl)-6-[5-({[2-(methylsulfonyl)ethyl]amino}methyl)-2-furanyl]-4-quinazolinamine 4-methylbenzenesulfonate hydrate as a bright yellow crystalline solid.

Example 3

Preparation of N-(3-chloro-4-[(3-fluorobenzyl)oxy]phenyl}-6-[5-({[2-(methane sulphonyl)ethyl]amino}methyl)-2-furyl]-4-quinazolinamine Tablets, 250 mg Table 4 contains a description of the components used in the preparation of a granulation mixture and Table 5 contains a description of the components used in the preparation of a compression blend for one embodiment of N-{3-Chloro-4-[(3-fluorobenzyl)oxy]phenyl}-6-[5-({[2-(methanesulphonyl)ethyl]amino}methyl)-2-furyl]-4-quinazolinamine Tablets, 250 mg for a batch size of 120,000 tablets.

TABLE 4

| Component | Amount (mg/tab)* | Amount (kg/batch)** | Function |
|---|---|---|---|
| Granulation Mixture | | | |
| Active[2] | 405 | 48.6 | Active |
| Microcrystalline Cellulose NF, PhEur, JP | 387 | 46.44 | Diluent Glidant |
| Povidone USP, PhEur, JP | 58.5 | 7.02 | Binder |
| Purified Water[2] | qs | qs | Granulating liquid |
| Total dry granules | 850.5 | 102.06 | |

[1]N-{3-Chloro-4-[(3-fluorobenzyl)oxy]phenyl}-6-[5-({[2-(methanesulphonyl)ethyl]amino}methyl)-2-furyl]-4-quinazolinamine. Prepared according to the procedure of Scheme B. The actual amount of drug substance may be adjusted based on the purity of the specific lot of drug substance included in the batch. The amount of diluent (microcrystalline cellulose) is then adjusted to maintain a core tablet weight of 900 mg.
[2]Removed during drying process.
*Based on theoretical drug substance factor of 1.62 = 1.00
**Quantities for a 120,000 tablet granulation.

TABLE 5

| Component | Amount (mg/tab) | Amount (kg/batch)* | Function |
|---|---|---|---|
| Compression Blend | | | |
| Granules[1] | 850.5 | 306.18 | Active Granules |
| Sodium Starch Glycolate | 40.5 | 14.58 | Disintegrant |
| Magnesium Stearate | 9 | 3.24 | Lubricant |
| Total Weight | 900.0 | 324.0 | |
| Coating | | | |
| Opadry ®/Orange YS-1-13065-A | 27.0 | 9.72 | Film Coat |
| Purified Water[2] | qs | qs | |
| Total Tablet Weight | 927.0 | 333.72 | |

[1]Granules prepared from Granular Mix of Table 4
[2]Removed during drying process
*360,000 Tablets For this example all ingredients were weighed to amounts which were consistent with the weight percents recited in Tables 4 and 5.

(i) Formation of Active Granules (Batch Size—120,000 Tablets)

N-{3-Chloro-4-[(3-fluorobenzyl)oxy]phenyl}-6-[5-({[2-(methanesulphonyl)ethyl]amino}methyl)-2-furyl]-4-quinazolin amine ditosylate monohydrate and microcrystalline cellulose NF, PH. Eur., JP were added to the bowl of a Glatt WSTCD 160/200 granulator. A 20% solution of povidone in water was prepared using a Lightnin' mixer with a suitable tank. The N-{3-Chloro-4-[(3-fluorobenzyl)oxy]phenyl}-6-[5-({[2-(methanesulphonyl)ethyl]amino}methyl)-2-furyl]-4-quinazolin amine ditosylate monohydrate and microcrystalline cellulose were fluidized in the Glatt WSTCD 160/200 bowl and spraying of the 20% povidone solution began immediately at approximately 2000 g/minute with an inlet air temperature of 58° C. The inlet air humidity was maintained below 10 g/kg. After the povidone solution was applied purified water was added as needed to obtain a proper granulation wetness. At the end of granulation the inlet air temperature was raised to 60° C. and drying was continued until an LOD of approximately 2.5% was reached. The dried active granules were passed through a Comil Model 196S cone mill fitted with a 0.075 inch round holed screen at approximately 1000 RPM.

Sieve analysis was performed and tapped density profiles established. Sieve analysis was performed using a Retsch sieve shaker, Model AS200 Digit. Approximately 20 g of active dried granules was placed on the top of a nest of tared sieves of 20, 30, 40, 60, 100, and 200 mesh. Shaking was done for 5 minutes at an amplitude setting of 60 with the pulse on. This sieve analysis revealed little batch to batch variation in particle size of the active granules. The granules were also characterized for Bulk Density (BD) and Tapped Density (TD). BD and TD of the granules was measured by adding a weighed amount of granules into a 100 ml graduated cylinder and measuring the volume initially and after 25, 50, 100, 200, 300, 500, and 1250 taps respectively.

(ii) Tablet Formation

A compression blend was formed by combining the prepared active granules and sodium starch glycolate in a bin which was transferred to a Bin blender where the ingredients were blended for 15 minutes @17 RPM. The bin was then removed from the tumble blender and magnesium stearate added to the blend of active granules and sodium starch glycolate. The bin was sealed and transferred back to the tumble blender and blended for 3 minutes @17 RPM to obtain the compression mix. Tablets were compressed from the compression blend using a Fette model 2090 rotary tablet press fitted with 19.05×10.41 mm standard concave tooling. The tablet press was adjusted to provide tablets with the following specifications.

| | |
|---|---|
| Weight of 10 tablets | 9.00 g |
| Weight Range of 10 tablets | 8.80-9.20 g |
| Individual Tablet Weight | 900.0 mg |
| Individual Weight Range | 855.0-945.0 mg |
| Target Average Tablet Hardness | 18 kp |
| Individual Hardness Range | 9-27 kp |
| Individual Thickness Range | 5.00-8.00 mm |
| Compression Speed Range | 40,000-100,000 tpm |

Uncoated tablets were characterized for weight, hardness, disintegration and dissolution. Tablets were weighed and hardness determined using, for example, a Dr. Schleuniger® Pharmatron Testlink Instrument available from Dr Schleuniger® Pharmatron of Solothurn, Switzerland. Disintegration was determined in 900 mL of water at 37° C. and drug dissolution was evaluated using a USP Type II apparatus at 55 rpm paddle speed in 900 ml of 0.1N HCl containing 2% w/w Tween 80 at 37° C.

The produced tablets were coated in a GLATT® 1500 coater using 12% w/w Orange Opadry®IYS-1-13065-A aqueous suspension at a pan speed of 5-7 rpm. Five spray nozzles (orifice opening-1.2 mm) were used to deliver coating solution at a total rate of 450-550 g/min. The airflow was maintained at 3800-4200 cmh with the outlet air temperature ranging from 50 to 70° C. The gun to bed distance was kept at 18-30 cm. Sufficient film coating was applied to achieve a 3 percent by weight gain assuming 100% coating efficiency.

Coated tablets were characterized for drug dissolution using a USP Type II apparatus at 55 rpm paddle speed in 900 ml of 0.1N HCl containing 2% w/w Tween 80 at 37° C.

Table 6 recites the tablet composition.

TABLE 6

| Component | Amount (mg/tab)[2] | Reference to Standard | Function |
|---|---|---|---|
| Active[1] | 405 | | Active |
| Microcrystalline Cellulose | 387 | EP, JPE, NF | Diluent |
| Povidone | 58.5 | EP, JP, USP | Binder |
| Purified Water[3] | qs | EP, JP, USP | Granulating liquid |
| Sodium Starch Glycolate | 40.5 | EP, JPE, USP | Disintegrant |
| Magnesium Stearate | 9.0 | EP, JPE, NF | Lubricant |
| Opadry ® YS-1-13065-A | 27 | N/A | Film coat |
| Purified Water[3] | qs | EP, JP, USP | Film coat solvent |
| Total tablet weight | 927 | | |

[1]N-{3-Chloro-4-[(3-fluorobenzyl) oxy]phenyl}-6-[5-({[2-(methanesulphonyl)ethyl] amino}methyl)-2-furyl]-4-quinazolinamine ditosylate monohydrate, equivalent to 250 mg [1]N-{3-Chloro-4-[(3-fluorobenzyl) oxy]phenyl}-6-[5-({[2-(methanesulphonyl)ethyl] amino}methyl)-2-furyl]-4-quinazolinamine.
[2]Theoretical core tablet weight is 900 mg.
[3]Removed during drying.

We claim:

1. An oral pharmaceutical formulation prepared by a process having the steps:

(a) admixing and fluidizing N-{3-Chloro-4-[(3-fluorobenzyl)oxy]phenyl}-6-[5-({[2-(methanesulphonyl)ethyl] amino}methyl)-2-furyl]-4-quinazolinamine ditosylate monohydrate and at least microcrystalline cellulose in a fluid bed granulator to form a fluidized mixture, wherein the N-{3-Chloro-4-[(3-fluorobenzyl)oxy]phenyl}-6-[5-({[2-(methanesulphonyl)ethyl] amino}methyl)-2-furyl]-4-quinazolinamine ditosylate monohydrate of the fluidized mixture is present in the range of 45 to 57 percent by weight, and the microcrystalline cellulose of the fluidized mixture is present in the range of 43 to 55 percent by weight;

(b) granulating said mixture utilizing an aqueous solution of at least povidone to form active granules, wherein the aqueous solution is a 10 to 25 percent solution of povidone in purified water;

(c) blending the active granules with at least sodium starch glycolate and at least magnesium stearate to form a compression blend, wherein the active granules are present in a range of 93 to 96 percent by weight, the sodium starch glycolate is present in a range of 3.5 to 5.5 percent by weight, and the magnesium stearate is present in a range of 0.8 to 1.2 percent by weight;

(d) compressing the compression blend into a tablet form; and (e) film coating the tablet.

* * * * *

UNITED STATES PATENT AND TRADEMARK OFFICE
CERTIFICATE OF CORRECTION

| | |
|---|---|
| PATENT NO. | : 8,821,927 B2 |
| APPLICATION NO. | : 11/911843 |
| DATED | : September 2, 2014 |
| INVENTOR(S) | : Carter et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1249 days.

Signed and Sealed this
Eighteenth Day of August, 2015

Michelle K. Lee
*Director of the United States Patent and Trademark Office*